US012636069B2

(12) United States Patent
Chung et al.

(10) Patent No.: US 12,636,069 B2
(45) Date of Patent: May 26, 2026

(54) SYSTEM AND METHOD TO AVOID CONTACT WITH HOT INSTRUMENT IN ROBOTIC SURGICAL SYSTEM

(71) Applicant: Cilag GmbH International, Zug (CH)

(72) Inventors: Scotty A. Chung, Cincinnati, OH (US); Mihir P. Joshi, Holland, OH (US); Matjaz Jogan, Philadelphia, PA (US)

(73) Assignee: CILAG GMBH INTERNATIONAL, Zug (CH)

( * ) Notice: Subject to any disclaimer, the term of this patent is extended or adjusted under 35 U.S.C. 154(b) by 268 days.

(21) Appl. No.: 18/343,794

(22) Filed: Jun. 29, 2023

(65) Prior Publication Data

US 2025/0000568 A1 Jan. 2, 2025

(51) Int. Cl.
| | |
|---|---|
| *A61B 18/14* | (2006.01) |
| *A61B 18/00* | (2006.01) |
| *A61B 34/32* | (2016.01) |
| *A61B 90/00* | (2016.01) |

(52) U.S. Cl.
CPC .......... *A61B 18/1442* (2013.01); *A61B 34/32* (2016.02); *A61B 90/37* (2016.02); *A61B 2018/00791* (2013.01); *A61B 2018/00898* (2013.01); *A61B 2090/365* (2016.02)

(58) Field of Classification Search
CPC ..... A61B 18/1442; A61B 34/32; A61B 34/30; A61B 90/37; A61B 2090/365; A61B 2018/00791; A61B 2018/00898; A61B 2034/301
USPC ......................................................... 606/34
See application file for complete search history.

(56) References Cited

U.S. PATENT DOCUMENTS

| | | | |
|---|---|---|---|
| 9,763,741 | B2 | 9/2017 | Alvarez et al. |
| 10,166,082 | B1 | 1/2019 | Hariri et al. |
| 10,464,209 | B2 | 11/2019 | Ho et al. |
| 10,667,875 | B2 | 6/2020 | DeFonzo et al. |
| 10,765,303 | B2 | 9/2020 | Graetzel et al. |
| 10,827,913 | B2 | 11/2020 | Ummalaneni et al. |
| 10,881,280 | B2 | 1/2021 | Baez, Jr. |
| 10,898,277 | B2 | 1/2021 | Srinivasan et al. |
| 11,058,493 | B2 | 7/2021 | Rafii-Tari et al. |
| 2018/0049832 | A1 * | 2/2018 | Eckert .................... A61B 34/30 |
| 2021/0298813 | A1 | 9/2021 | Scheib |

(Continued)

FOREIGN PATENT DOCUMENTS

| | | | | |
|---|---|---|---|---|
| WO | WO-2015026562 A1 * | 2/2015 | ............. | G16Z 99/00 |
| WO | WO-2020260999 A1 * | 12/2020 | ............. | A61B 90/08 |

*Primary Examiner* — Beverly M Flanagan
(74) *Attorney, Agent, or Firm* — FBT GIBBONS LLP

(57) ABSTRACT

A system includes a robotic arm, an instrument, and a control module. The control module is operable to drive movement of the robotic arm to thereby move the instrument relative to the patient. The control module is configured to monitor one or more parameters indicative of a temperature of a portion of the end effector of the instrument; to determine whether the temperature of the portion of the end effector crosses a threshold value, based at least in part on the one or more monitored parameters; and to restrict movement of the end effector in response to determining that the temperature of the portion of the end effector crosses the threshold value. The restricted movement may include removal of the end effector from the patient or movement of the end effector after removal of the end effector from the patient.

19 Claims, 12 Drawing Sheets

(56)          References Cited

U.S. PATENT DOCUMENTS

| | | | |
|---|---|---|---|
| 2021/0298815 A1 | 9/2021 | Scheib | |
| 2021/0298852 A1 | 9/2021 | Crosetti et al. | |
| 2023/0277249 A1* | 9/2023 | Bork ..................... | A61B 34/20 |
| | | | 600/424 |

\* cited by examiner

300 ACTIVATE END EFFECTOR OF INSTRUMENT IN PATIENT

302 RECEIVE COMMAND TO REMOVE INSTRUMENT FROM PATIENT

304 DETERMINE END EFFECTOR TEMPERATURE

306 END EFFECTOR SAFE FOR REMOVAL?

Y

308 ALLOW REMOVAL

N

310 PROVIDE USER FEEDBACK

312 PREVENT REMOVAL

600  ACTIVATE END EFFECTOR OF INSTRUMENT IN PATIENT

602  DETERMINE END EFFECTOR TEMPERATURE

604  END EFFECTOR SAFE FOR MANUAL REMOVAL?

N

Y

606  PREVENT MANUAL REMOVAL

608  ALLOW MANUAL REMOVAL

SYSTEM AND METHOD TO AVOID CONTACT WITH HOT INSTRUMENT IN ROBOTIC SURGICAL SYSTEM

BACKGROUND

A variety of medical instruments may be used in procedures conducted by a medical professional operator, as well as applications in robotically assisted surgeries. In the case of robotically assisted surgery, the clinician may operate a master controller to remotely control the motion of such medical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the medical instrument. In some scenarios, a servo motor moves a manipulator supporting the medical instrument based on the clinician's manipulation of the hand input devices. During the medical procedure, the clinician may employ, via a robotic system, a variety of medical instruments including an ultrasonic blade, a surgical stapler, a tissue grasper, a needle driver, an electrosurgical cautery probe, etc. Each of these structures performs functions for the clinician, for example, cutting tissue, coagulating tissue, holding or driving a needle, grasping a blood vessel, dissecting tissue, or cauterizing tissue.

Examples of robotic systems are described in U.S. Pat. No. 9,763,741, entitled "System for Robotic-Assisted Endolumenal Surgery and Related Methods," issued Sep. 19, 2017, the disclosure of which is incorporated by reference herein, in its entirety; U.S. Pat. No. 10,464,209, entitled "Robotic System with Indication of Boundary for Robotic Arm," issued Nov. 5, 2019, the disclosure of which is incorporated by reference herein, in its entirety; U.S. Pat. No. 10,667,875, entitled "Systems and Techniques for Providing Multiple Perspectives During Medical Procedures," issued Jun. 2, 2020, the disclosure of which is incorporated by reference herein, in its entirety; U.S. Pat. No. 10,765,303, entitled "System and Method for Driving Medical Instrument," issued Sep. 8, 2020, the disclosure of which is incorporated by reference herein, in its entirety; U.S. Pat. No. 10,827,913, entitled "Systems and Methods for Displaying Estimated Location of Instrument," issued Nov. 10, 2020, the disclosure of which is incorporated by reference herein, in its entirety; U.S. Pat. No. 10,881,280, entitled "Manually and Robotically Controllable Medical Instruments," issued Jan. 5, 2021, the disclosure of which is incorporated by reference herein, in its entirety; U.S. Pat. No. 10,898,277, entitled "Systems and Methods for Registration of Location Sensors," issued Jan. 26, 2012, the disclosure of which is incorporated by reference herein, in its entirety; and U.S. Pat. No. 11,058,493, entitled "Robotic System Configured for Navigation Path Tracing," issued Jul. 13, 2021, the disclosure of which is incorporated by reference herein, in its entirety.

Some robotic surgical systems may process thermal information. Examples of such systems are described in U.S. Pub. No. 2021/0298813, entitled "Systems and Methods of Communicating Thermal Information for Surgical Robotic Devices," published Sep. 30, 2021, now abandoned, the disclosure of which is incorporated by reference herein, in its entirety; U.S. Pub. No. 2021/0298815, entitled "Systems and Methods of Communicating Thermal Information for Surgical Robotic Devices," published Sep. 30, 2021, the disclosure of which is incorporated by reference herein, in its entirety; and U.S. Pub. No. 2021/0298852, entitled "Systems and Methods of Communicating Thermal Information for Surgical Robotic Devices," published Sep. 30, 2021, now abandoned, the disclosure of which is incorporated by reference herein, in its entirety.

While several medical instruments, systems, and methods have been made and used, it is believed that no one prior to the inventors has made or used the invention described in the appended claims.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

I. OVERVIEW OF EXAMPLE OF ROBOTIC SURGICAL SYSTEM

Figure 1:
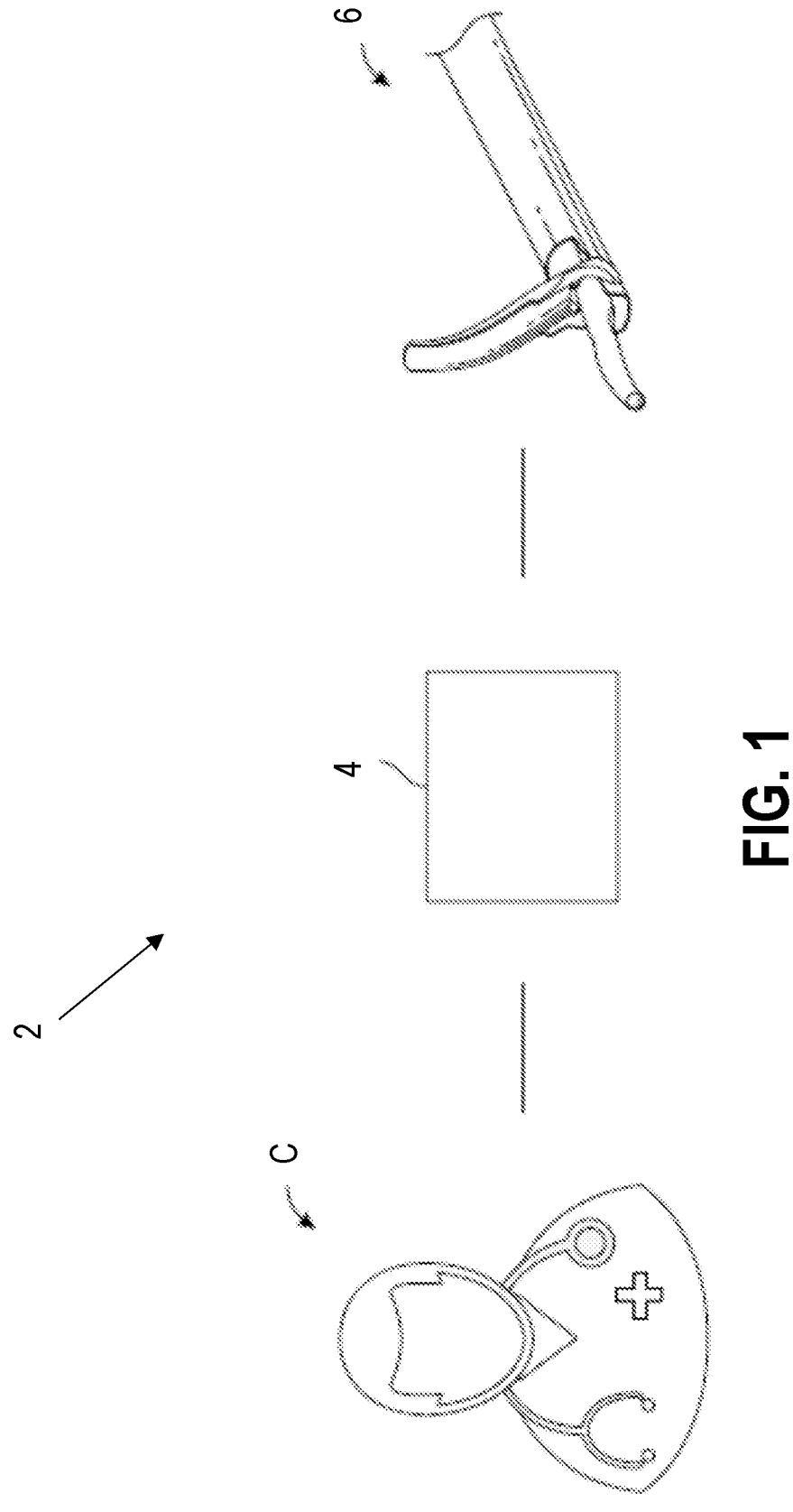
FIG. 1 depicts a schematic view of an example of a robotic surgical environment.

FIG. 1 shows an example of a robotic surgical environment (2). Robotic surgical environment (2) includes a clinician (C), a robotic surgical system (4), and a surgical instrument (6). While one clinician (C) is shown, it should be understood that two or more clinicians (C) may be present within robotic surgical environment (2), including one or more surgeons, one or more nurses, etc. The clinician (C) may interact with robotic surgical system (4) to thereby operate one or more surgical instruments (6) on and/or within a patient. Examples of forms that may be taken by robotic surgical system (4) and surgical instrument (6) will be described in greater detail below.

Robotic surgical environment (2) may be provided in a variety of different medical procedures, including both minimally invasive, such as laparoscopy, and non-invasive, such as endoscopy, procedures. Among endoscopy procedures, robotic surgical environment (2) may be provided in the context of bronchoscopy, ureteroscopy, gastroscopy, etc. In addition to being used in a variety of procedures, robotic surgical environment (2) may provide additional benefits, such as enhanced imaging and guidance to assist the clinician (C). Additionally, robotic surgical environment (2) may provide the clinician (C) with the ability to perform the procedure from an ergonomic position without the need for awkward arm motions and positions. Still further, robotic surgical environment (2) may provide the clinician (C) with the ability to perform the procedure with improved ease of use such that one or more of the instruments (6) of the system can be controlled by a single user.

A. Example of Robotic System Table

Figure 2:
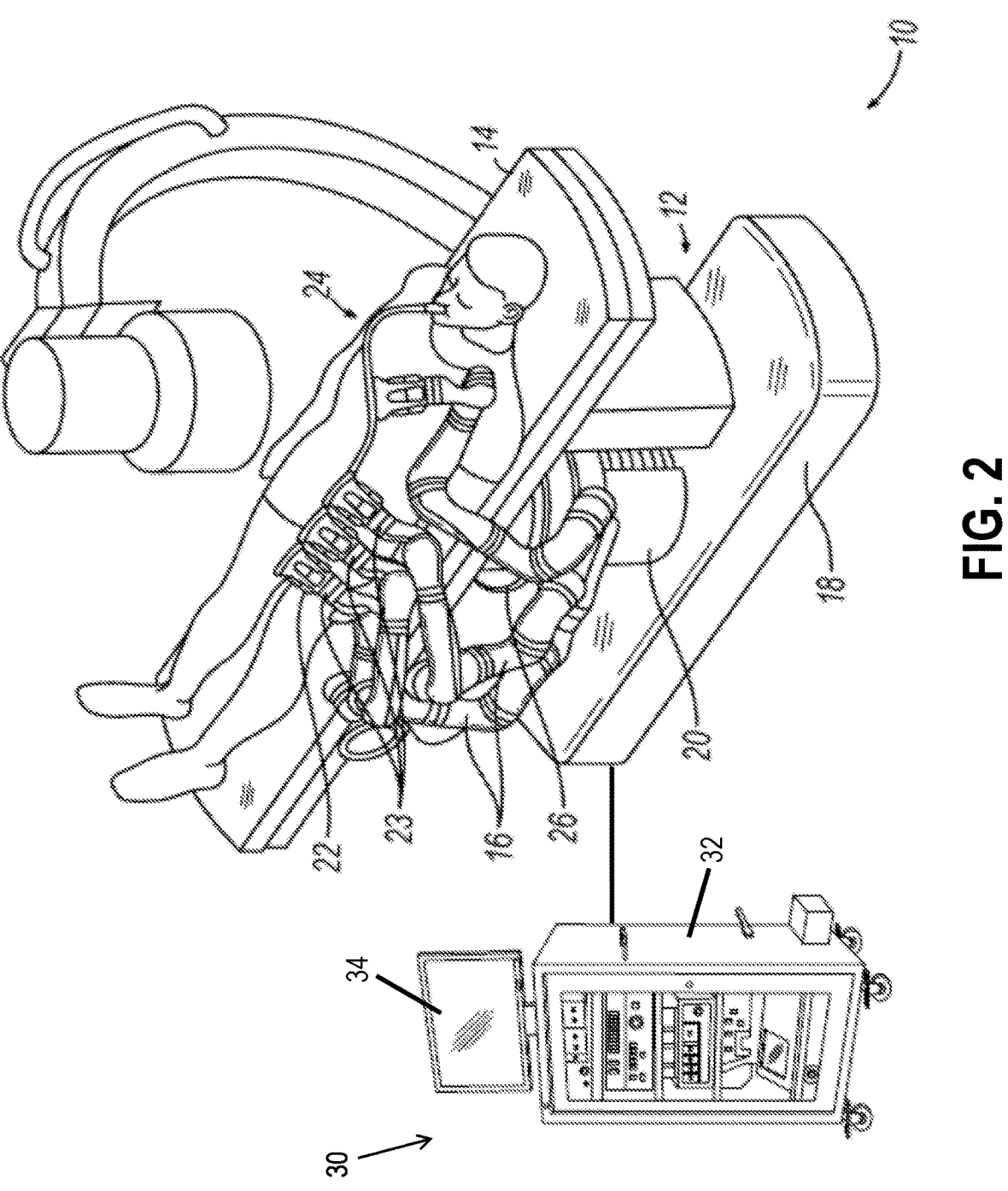
FIG. 2 depicts a perspective view of an example of a robotic surgical system that may be incorporated into the robotic surgical environment of FIG. 1.

FIG. 2 illustrates an example of a form that may be taken by robotic surgical system (2). In particular, FIG. 2 shows a robotic surgical system (10) that includes a support structure (12) for supporting a platform (14) (shown as a "table" or "bed") over the floor, one or more robotic arms (16), and a console unit (30). Support structure (12) includes a base (18) and a column (20). Column (20) structurally supports platform (14) and provides a path for vertical translation of robotic arms (16) relative to base (18). In some versions, base (18) may stow and store robotic arms (16) when not in use. Column (20) of the present example also includes a ring-shaped carriage (26), from which robotic arms (16) extend. A control module (32) of console unit (30) is coupled with robotic surgical system (10). While four robotic arms (16) are shown, more or fewer robotic arms (16) are envisioned.

Robotic arms (16) are shown as part of a table-mounted system, but in other configurations, robotic arms (16) may be mounted in a cart, ceiling or sidewall, or other suitable support surface. While robotic arms (16) are shown as extending from column (20) via carriage (26), robotic arms (16) may alternatively be coupled with robotic surgical system (10) using a variety of suitable structures. While robotic arms (16) are all shown as being positioned on one side of the patient in FIG. 2, other configurations may position robotic arms (16) on both sides of the patient, between the legs of the patient, and/or in any other suitable locations. Tool drivers (22) are positioned at distal ends of robotic arms (16) in the present example. Tool drivers (22) are operable to manipulate one or more surgical instruments (24), as will be described in greater detail below.

Control module (32) may include one or more of a programmable processor, a programmable controller, a microprocessor, a microcontroller, a graphics processing unit (GPU), a digital signal processor (DSP), a reduced-instruction set computer (RISC), an application specific integrated circuit (ASIC), a field programmable gate array (FPGA), a field programmable logic device (FPLD), a logic circuit, and/or another logic-based device executing various functions including the ones described herein. Control module (32) may also include one or more memory devices such as one or more of a semiconductor memory, a magnetically readable memory, an optical memory, a hard disk drive (HDD), an optical storage drive, a solid-state storage device, a solid-state drive (SSD), a flash memory, a read-only memory (ROM), erasable programmable read-only memory (EPROM), electrically erasable programmable read-only memory (EEPROM), a random-access memory (RAM), a non-volatile RAM (NVRAM) memory, a compact disc (CD), a compact disc read-only memory (CD-ROM), a digital versatile disk (DVD), a Blu-ray disk, a redundant array of independent disks (RAID) system, a cache and/or any other storage device or storage disk in which information is stored for any duration (e.g., permanently, temporarily, for extended periods of time, for buffering, for caching).

In addition to including control module (32), console unit (30) of the present example includes a display screen (34) and may comprise various user input devices, and/or various other features. While only one console unit (30) is shown, some variations of robotic surgical system (10) may include more than one console unit. For instance, some variations may include a tower-like console unit similar to the console unit (30) depicted in FIG. 2, with the tower-like console unit being interacted with by a first clinician (C) who is primarily standing; and another console unit that is interacted with by a second clinician who is primarily sitting. Alternatively, console unit (30) may be provided in any suitable number, configuration, or arrangement.

B. Example of a Robotic Arm Assembly

Figure 3:
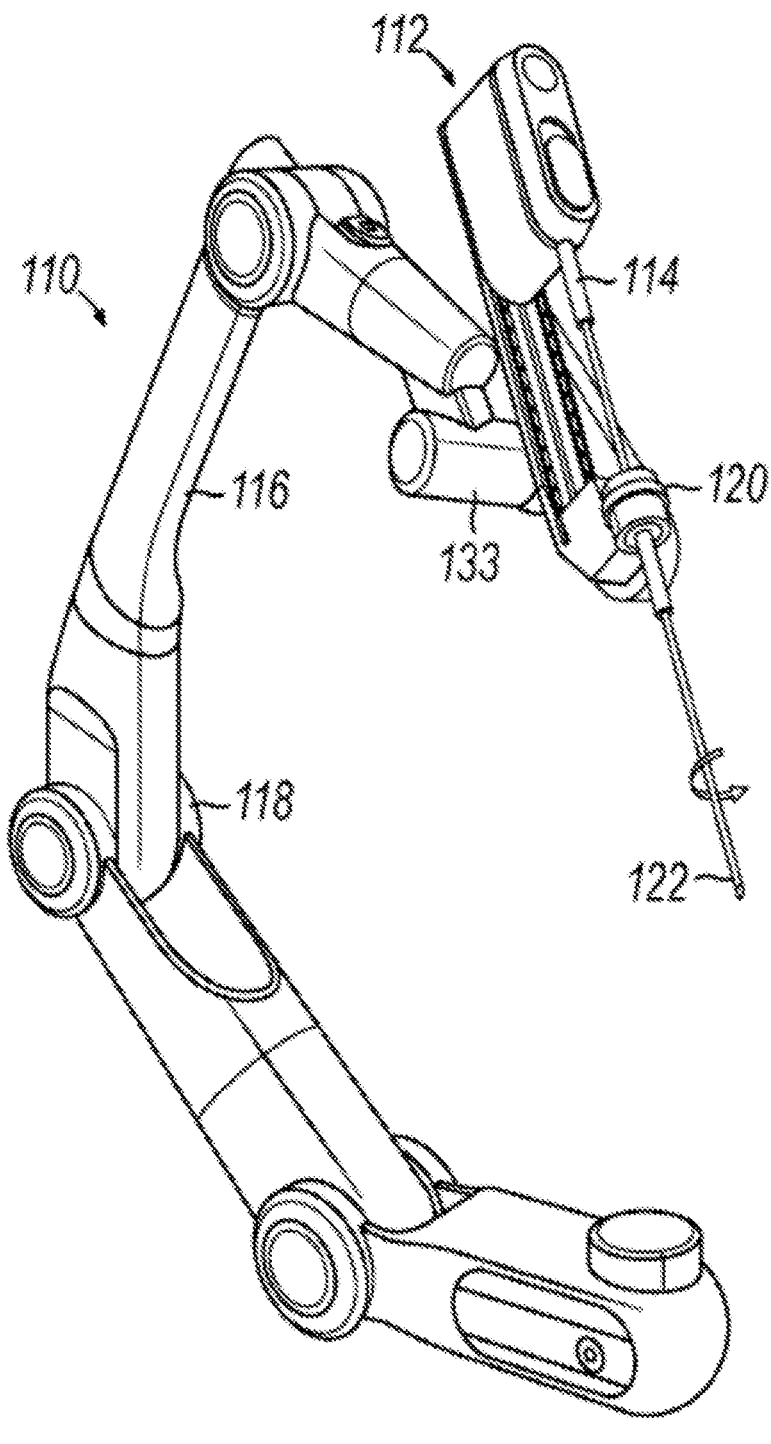
FIG. 3 depicts a perspective view of an example of a robotic arm, an example of a tool drive, and a first example of a surgical instrument, each configured for use with the robotic surgical system of FIG. 2.

FIG. 3 shows an example of a robotic arm (110), a tool driver (112), and a surgical instrument (114), which may be incorporated into robotic surgical system (10) in place of a robotic arm (16), a tool driver (22), and a surgical instrument (24) that are shown in FIG. 2. Additional examples of robotic arms, tool drivers, and surgical instruments are shown and described in U.S. Pat. No. 10,166,082, entitled "System and Method for Controlling a Robotic Wrist," issued Jan. 1, 2019, the disclosure of which is incorporated by reference herein, in its entirety.

As shown in FIG. 3, robotic arm (110) includes a plurality of links (116) and a plurality of joints (118) for actuating links (116) relative to one another. Tool driver (112) is attached to the distal end of robotic arm (110). Tool driver (112) includes a cannula (120) coupled to the end of tool driver (112), to receive and guide surgical instrument (114). Surgical instrument (114) may include an endoscope, a laparoscope, a stapler, graspers, an ultrasonic instrument, a radiofrequency (RF) electrosurgical instrument, or any other suitable kind of instrument. Surgical instrument (114) is inserted into the patient via cannula (120). The distal end of surgical instrument (114) includes an end effector (122). End effector (122) is configured to interact with the patient (e.g., providing visualization, stapling, grasping, ultrasonic cutting and/or sealing, electrosurgical cutting and/or sealing, etc.).

Joints (118) of robotic arm (110) may be actuated to selectively position and orient tool driver (112), which actuates the end effector (122) for robotic surgeries. Joints (118) may include various types, such as a pitch joint or a roll joint, which may substantially constrain the movement of the adjacent links (116) around certain axes relative to other links (116). Each joint (118) represents an independent degree of freedom available to robotic arm (110). A multitude of joints (118) result in a multitude of degrees of freedom, allowing for "redundant" degrees of freedom. Redundant degrees of freedom allow the robotic arms (110) to position their respective end effectors (122) at a specific position, orientation, and trajectory in space using different positions links (116) and angles of joints (118). This allows for the system to position and direct a surgical instrument (114) from a desired point in space while allowing the clinician to move joints (118) into a clinically advantageous position away from the patient to create greater access, while avoiding collisions of robotic arms (110).

II. EXAMPLES OF SURGICAL INSTRUMENTS

A. Example of an Electrosurgical Instrument

Figure 4:
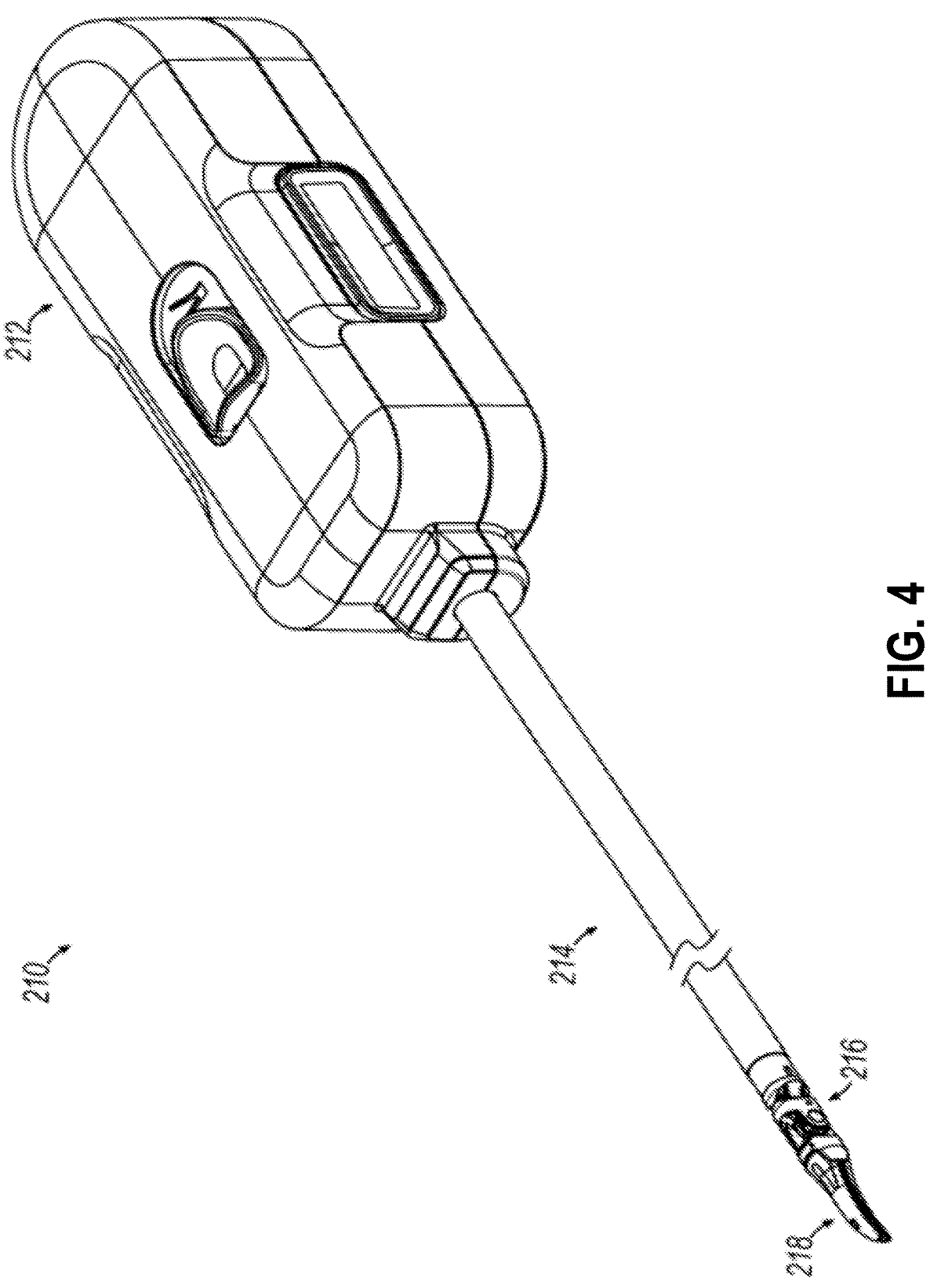
FIG. 4 depicts a perspective view of a second example of a surgical instrument configured for use with the robotic surgical system of FIG. 2.

FIG. 4 shows an example of a surgical instrument (210) configured for use with robotic surgical system (10) including robotic arms (16, 110) and tool drivers (22, 112) of FIGS. 2-3. Surgical instrument (210) may be used in place of surgical instrument (6, 24, 114). Surgical instrument (210) includes a body (shown as a tool drive adapter (212)), a shaft assembly (214), an articulation section (216) of shaft assembly (214), and an end effector (218).

Figure 5:
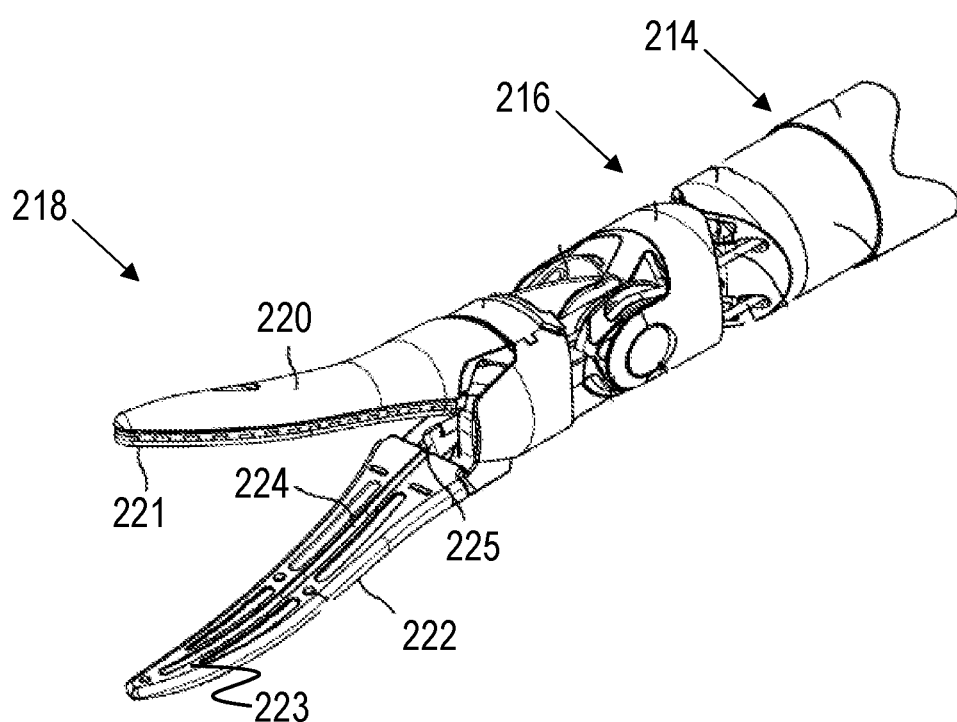
FIG. 5 depicts an enlarged perspective view of a distal end portion of the surgical instrument of FIG. 4, with an end effector in an open configuration and an articulation section in a straight configuration.

As shown in FIG. 5, end effector (218) includes an upper jaw (220) having an upper electrode surface (221), a lower jaw (222) having a lower electrode surface (223), and a knife member (225) slidably disposed within a knife channel (224) cooperatively defined by upper jaw (220) and lower jaw (222). End effector (218) of the current example is configured to grasp tissue between jaws (220, 222), seal the tissue by applying bipolar RF energy to tissue via electrodes (221, 223), and sever the tissue via knife member (225). Upper jaw (220) and lower jaw (222) are pivotally coupled to each other such that jaws (220, 222) may actuate between an open configuration and a closed configuration in order to grasp tissue. Articulation section (216) extends between end effector (218) and shaft assembly (214). Articulation section (216) is configured to articulate pitch and yaw relative to deflect end effector (218) respectively through a pitch plane and a yaw plane.

While jaws (220, 222) are in the closed configuration, knife member (225) may be driven distally along a path defined by knife channel (224), from a proximal position to a distal position, in order to sever tissue grasped by jaws (220, 222). Once knife member (225) reaches the distal position within knife channel (224) in order to suitably sever tissue, knife member (225) may then be retracted within knife channel (224) back into the proximal position.

Electrode surfaces (221, 223) may be activated during any suitable time at which jaws (220, 222) interact with tissue in order to apply bipolar RF energy to tissue. For example, electrode surfaces (221, 223) may be activated after knife member (225) severs tissue in order to seal the recently severed tissue grasped between jaws (220, 222). As another illustrative example, electrode surfaces (221, 223) may be activated prior to knife member (225) severing tissue. As yet another illustrative example, electrode surface (221, 223) may be activated in order to cauterize tissue without cutting tissue.

In the current example, electrode surface (221) is an electrode body attached on the underside of jaw (220); while jaw (222) is formed from a suitable material in order to act as electrode surface (223). For example, jaw (222) may be formed of a metal material and be in connection with a ground wire; while electrode body forming electrode surface (221) is attached the underside of jaw (220) and in communication with a hot wire. Electrical power for electrode surfaces (221, 223) may be generated by a power source in control module (32) or by some other power source. Once suitably activated, RF energy may be transmitted between electrode surfaces (221, 223) in order to further transmit such RF energy through tissue that is between electrode surfaces (221, 223). Electrode surfaces (221, 223) may have any suitable configuration as would be apparent to one skilled in the art in view of the teachings herein. While in the current example, electrode surfaces (221, 223) are configured to deliver bipolar RF energy to tissue, it should be understood that end effector (218) may be configured to deliver any other suitable type of therapeutic energy to tissue as would be apparent to one skilled in the art in view of the teachings herein.

B. Example of an Ultrasonic Surgical Instrument

Figure 6:
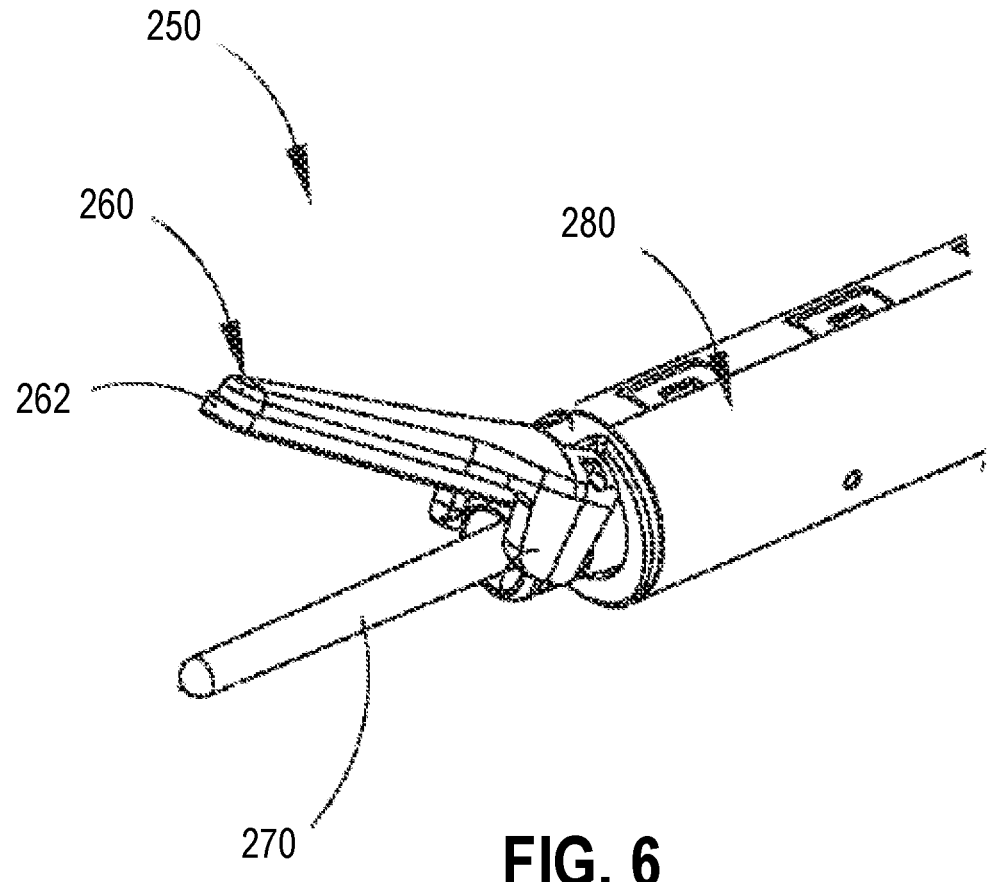
FIG. 6 depicts an enlarged perspective view of a distal end portion of another example of a surgical instrument configured for use with the robotic surgical system of FIG. 2, with an end effector in an open configuration.

FIG. 6 shows another example of an end effector (250) that may be incorporated into a surgical instrument (6, 24, 114, 210) that is driven by a robotic arm (16, 110). End effector (250) of this example comprises a clamp arm (260) and an ultrasonic blade (270), both of which extend distally from a shaft assembly (280). Clamp arm (260) includes a clamp pad (262) facing ultrasonic blade (270). Clamp arm (260) is pivotable toward and away from ultrasonic blade (270) to thereby cooperate with ultrasonic blade (270) to grasp tissue; and/or to compress tissue against ultrasonic blade (270). Ultrasonic blade (270) is acoustically coupled with an ultrasonic transducer (not shown) via an ultrasonic waveguide (not shown), such that the ultrasonic transducer is operable to drive ultrasonic blade (270) to oscillate at a resonant ultrasonic frequency. Thus, when tissue is compressed between ultrasonic blade (270) and clamp pad (262), the ultrasonic oscillation of ultrasonic blade (270) may simultaneously sever the tissue and denature the proteins in adjacent tissue cells, thereby providing a coagulative effect with relatively little thermal spread.

The ultrasonic transducer that drives oscillation of ultrasonic blade (270) may be powered by control module (32) or by some other power source. In some versions, an electrical current may also be provided through ultrasonic blade (270) and clamp arm (260) to also cauterize the tissue. For instance, ultrasonic blade (270) and clamp arm (260) may be configured to apply RF electrosurgical energy to tissue in addition to being configured to apply ultrasonic energy to tissue. Thus, some end effector variations may combine functionalities of end effectors (218, 250).

III. EXAMPLES OF TEMPERATURE-BASED CONTROL RESTRICTION AND FEEDBACK

In some instances, one or more features of an end effector that is configured and operable like either of end effectors (218, 250) may tend to substantially heat up during use. For instance, in the case of end effector (218), electrode surfaces (221, 223) may tend to heat up after being activated to apply RF electrosurgical energy to tissue a certain number of times and/or for a certain duration of time. In the case of end effector (250), ultrasonic blade (270) may tend to substantially heat up after being activated to apply ultrasonic energy to tissue a certain number of times and/or for a certain duration of time. It is contemplated that other kinds of end effectors may also tend to substantially heat up during use. Alternatively, some kinds of end effectors (e.g., cryoablation end effectors) may become substantially cold during use.

In any of the scenarios outlined above, it may be desirable for targeted to tissue to contact the end effector at the substantially high (or substantially low) temperature as the end effector intentionally engages the targeted tissue. However, it may also be desirable to avoid having the end effector inadvertently contact other, non-targeted tissue, as such unintentional contact with non-targeted may cause undesirable trauma or other effects on non-targeted tissue. Similarly, it may be desirable to avoid having a substantially hot (or substantially cold) end effector come into contact with other instrumentation or with a clinician (C).

The risk of inadvertent contact between a substantially hot (or substantially cold) end effector and non-targeted tissue, other instrumentation, or a clinician (C) may be particularly pronounced when end effector (218, 250) is being removed from the patient and/or otherwise being moved away from the patient. By way of example only, a clinician (C) may wish to remove end effector (218, 250) from the patient in order to remove a surgical instrument (6, 24, 114, 210) from a robotic arm (16, 110), to replace the removed surgical instrument (6, 24, 114, 210) with another instrument.

In some cases, the removal of end effector (218, 250) from the patient and/or other movement of end effector (218, 250) may be driven robotically by the clinician via control module (32). It may therefore be desirable to program control module (32) with a control algorithm that will prevent, or at least reduce the risk, of a substantially hot (or substantially cold) end effector (218, 250) from contacting non-targeted tissue, other instrumentation, or a clinician (C) when end effector (218, 250) is being removed from the patient. Similarly, it may be desirable to program control module (32) with a control algorithm that will prevent, or at least reduce the risk, of a substantially hot (or substantially cold) end effector (218, 250) from contacting non-targeted tissue, other instrumentation, or a clinician (C) shortly after end effector (218, 250) has been removed from the patient; at least while end effector (218, 250) is above a certain temperature threshold (or below a certain temperature threshold in the case of cryogenic end effectors, etc.). This may be particularly desirable to avoid injury to a clinician (C) who is trying to replace surgical instrument (6, 24, 114, 210) on a robotic arm (16, 110) when end effector (218, 250) of that surgical instrument (6, 24, 114, 210) is still substantially hot (or substantially cold).

Figure 7:
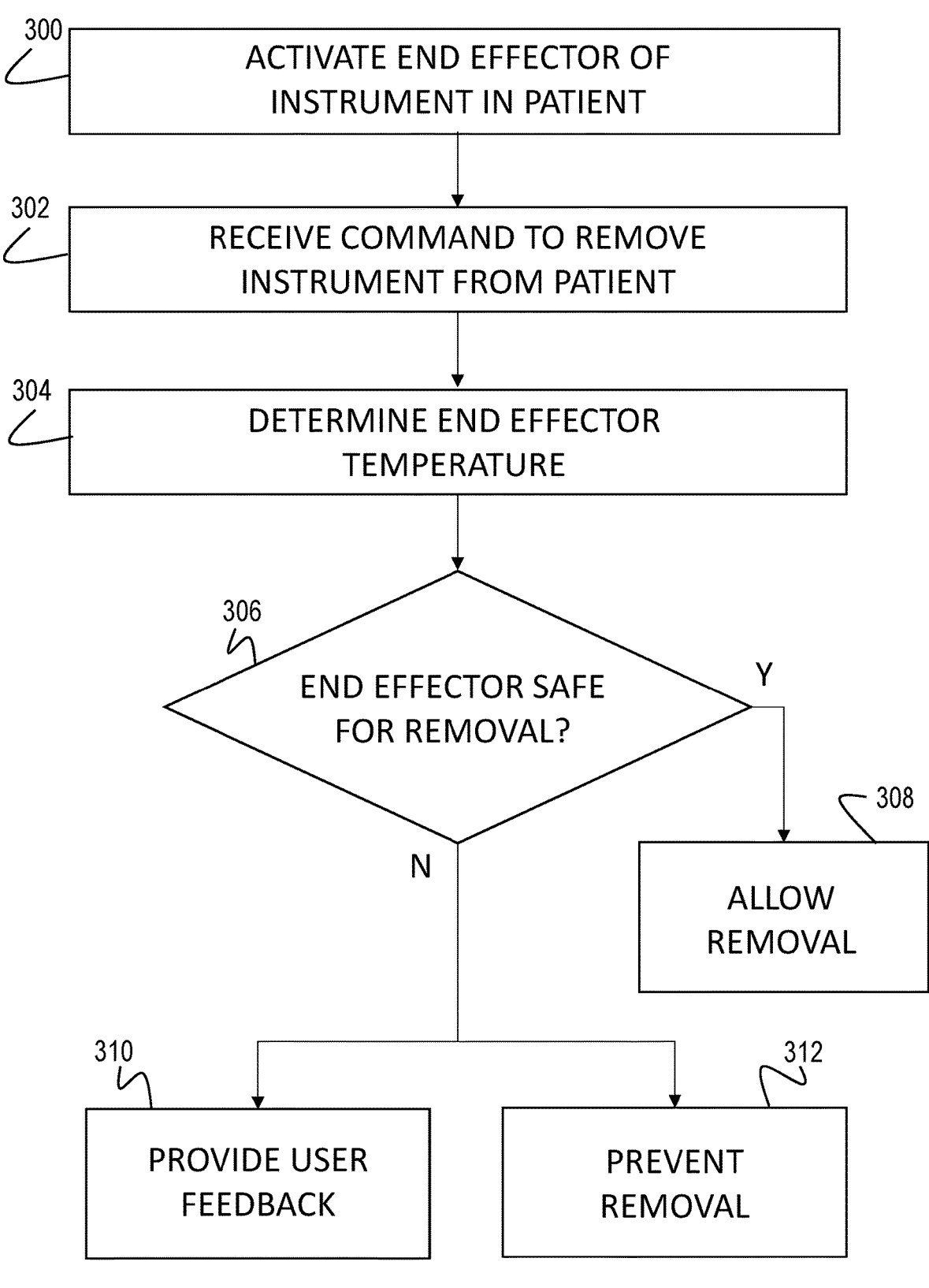
FIG. 7 depicts a flow chart showing an example of a control algorithm that may be executed by the robotic surgical system of FIG. 2.

FIG. 7 shows an example of an algorithm that may be executed, at least in part, by control module (32) during operation of robotic surgical system (10). While the algorithm and method of operation of FIG. 7 are described herein in the context of robotic surgical system (10) described above, the same algorithm and method of operation (and variations thereof) may be carried out via other kinds of robotic surgical systems (10). In this example, the method of operation begins with end effector (218, 250) being activated (block 300) within the patient. As noted above, this may include applying RF electrosurgical energy to tissue, applying ultrasonic energy to tissue, applying a combination of RF and ultrasonic energy to tissue, or applying some other form of energy to tissue. As also noted above, this may eventually result in substantial heating of end effector (218, 250) (or substantial cooling of an end effector).

Next, control module (32) receives (block 302) a command from a clinician (C) to remove end effector (218, 250) from the patient. In response to receiving (block 302) this command, control module (32) may then determine (block 304) the temperature of end effector (218, 250). This determination (block 304) may be carried out in various ways. For instance, some versions of end effector (218, 250) may include one or more temperature sensors (e.g., thermocouples, etc.), and control module (32) may receive signals from such temperature sensors to determine the temperature of end effector (218, 250). As another variation, control module (32) may track the duration, frequency, power level, and/or other operational parameters associated with the activation (block 300) of end effector (218, 250) during the procedure at hand; and calculate an approximate temperature of end effector (218, 250). Alternatively, control module (32) may determine (block 304) the temperature of end effector (218, 250) in any other suitable fashion.

After determining (block 304) the temperature of end effector (218, 250), control module (32) may determine (block 306) whether it is safe to remove end effector (218, 250) from the patient. This determination (block 306) may be performed by comparing the determined (block 304) temperature of end effector (218, 250) against a predetermined threshold; or may be performed on any other basis. For instance, in cases where end effector (218, 250) tends to operate at substantially high temperatures (e.g., after applying RF electrosurgical energy or ultrasonic energy, etc.), then control module (32) may determine (block 306) whether the determined (block 304) temperature of end effector (218, 250) exceeds a threshold. In cases where end effector (122) tends to operate at substantially low temperatures (e.g., after applying cryogenic energy, etc.), then control module (32) may determine (block 306) whether the determined (block 304) temperature of end effector (122) falls below a threshold. If control module (32) determines (block 306) that it is safe to remove end effector (218, 250) from the patient, then control module (32) may allow (block 308) end effector (218, 250) to be removed from the patient.

If control module (32) determines (block 306) that it is not safe to remove end effector (218, 250) from the patient, then control module (32) may provide (block 310) user feedback to the clinician (C) indicating that the temperature of end effector (218, 250) renders end effector (218, 250) unsafe for free removal. The clinician may then wait until the temperature of end effector (218, 250) reaches a temperature making it safe to remove end effector (218, 250) from the patient. To that end, control module (32) may continuously loop back to determining (block 304) the real-time temperature of end effector (218, 250), determining (block 306) whether that temperature is safe for removal of end effector (218, 250) from the patient, and either allow (block 308) removal or maintain providing (block 310) user feedback to the physician indicating that it is not yet safe to remove end effector (218, 250) from the patient. The user feedback may include audible feedback, haptic feedback (e.g., via a user input device of control module (32)), and/or visual feedback. Examples of forms that visual user feedback may take are described in greater detail below.

In addition to providing (block 310) user feedback, or in lieu of providing (block 310) user feedback, control module (32) may prevent (block 312) removal of end effector (218, 250) from the patient in response to determining (block 306) that it is not safe to remove end effector (218, 250) from the patient. For instance, control module (32) may simply ignore or otherwise not carry out instructions from the clinician (C) to remove end effector (218, 250) from the patient to prevent (block 312) removal of end effector (218, 250) from the patient. As noted above, control module (32) may continuously loop back to determining (block 304) the real-time temperature of end effector (218, 250), determining (block 306) whether that temperature is safe for removal of end effector (218, 250) from the patient, and either allow (block 308) removal or maintain preventing (block 312) removal of end effector (218, 250) from the patient.

In some cases, control module (32) may simply apply a waiting period before automatically transitioning from preventing (block 312) removal of end effector (218, 250) from the patient to allowing (block 308) removal of end effector (218, 250) from the patient. The duration of this waiting period may be predetermined or may be calculated based on the determined (304) temperature of end effector (218, 250). In such cases, it may not be necessary to continuously loop back to determining (block 304) the real-time temperature of end effector (218, 250), then determining (block 306) whether that temperature is safe for removal of end effector (218, 250) from the patient.

As also noted above, control module (32) may provide (block 310) user feedback to the clinician (C) while also preventing (block 312) removal of end effector (218, 250) from the patient. Alternatively, control module (32) may simply provide (block 310) user feedback to the clinician (C) without also preventing (block 312) removal of end effector (218, 250) from the patient. The clinician (C) may thus choose to disregard the user feedback and nevertheless remove end effector (218, 250) from the patient. As another alternative, control module (32) may prevent (block 312) the removal of end effector (218, 250) without also providing (block 310) user feedback to the clinician (C). In cases where control module (32) prevents (block 312) removal of end effector (218, 250) from the patient in response to determining (block 306) that the temperature of end effector (218, 250) renders end effector (218, 250) unsafe for free removal from the patient, some variations may nevertheless allow the clinician (C) to override this preventing (block 312) by providing further user input clearly indicating an intent to override. Such override may be necessary in some emergency situations where immediate removal of end effector (218, 250) from the patient is a higher safety priority than preventing inadvertent contact between end effector (218, 250) and either non-targeted tissue, other instrumentation, or the clinician.

A. Example of On-Screen Feedback

Figure 8A:
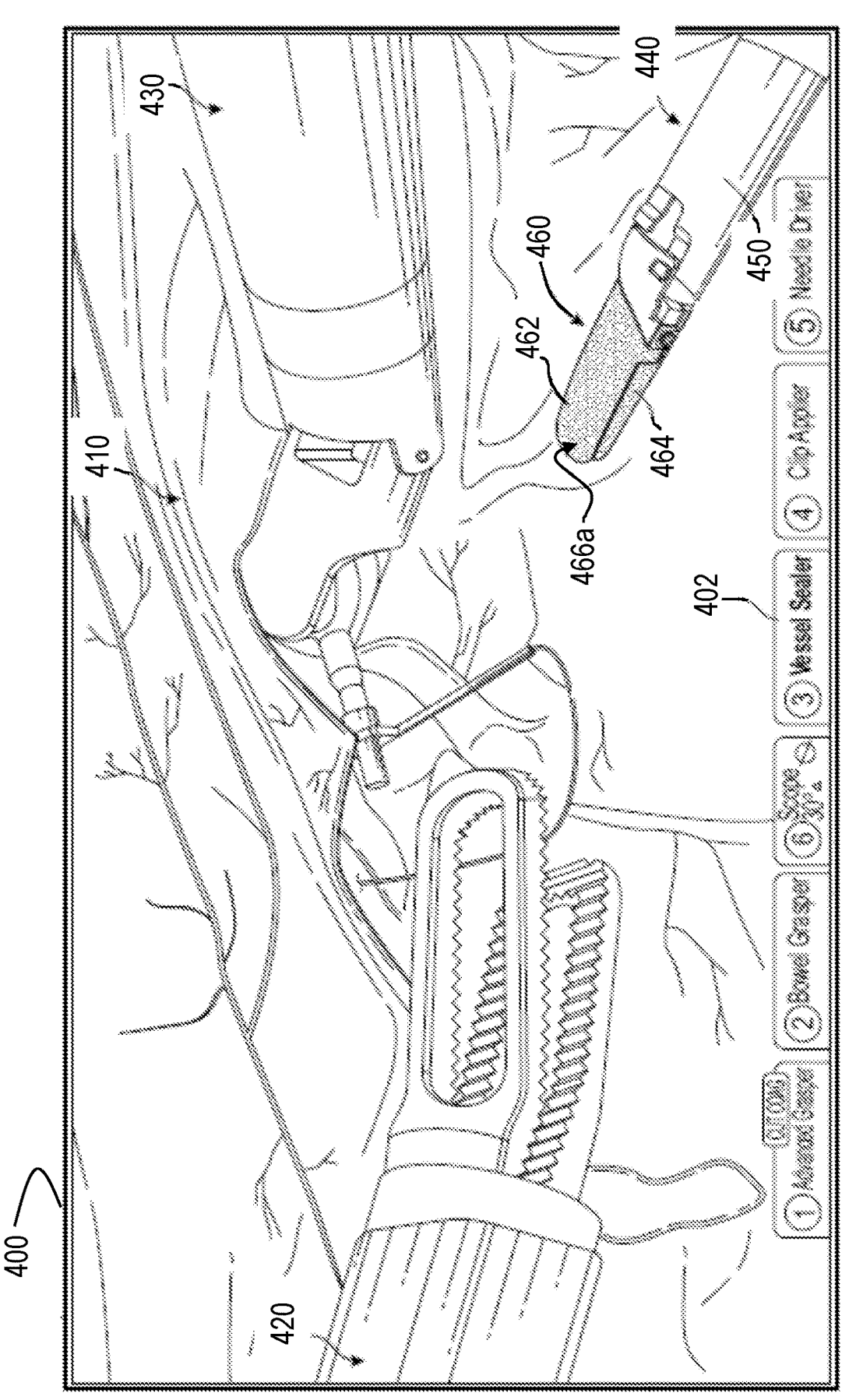
FIG. 8A depicts an example of a display that may be rendered by the robotic surgical system of FIG. 2 in a first state of operation.
Figure 8B:
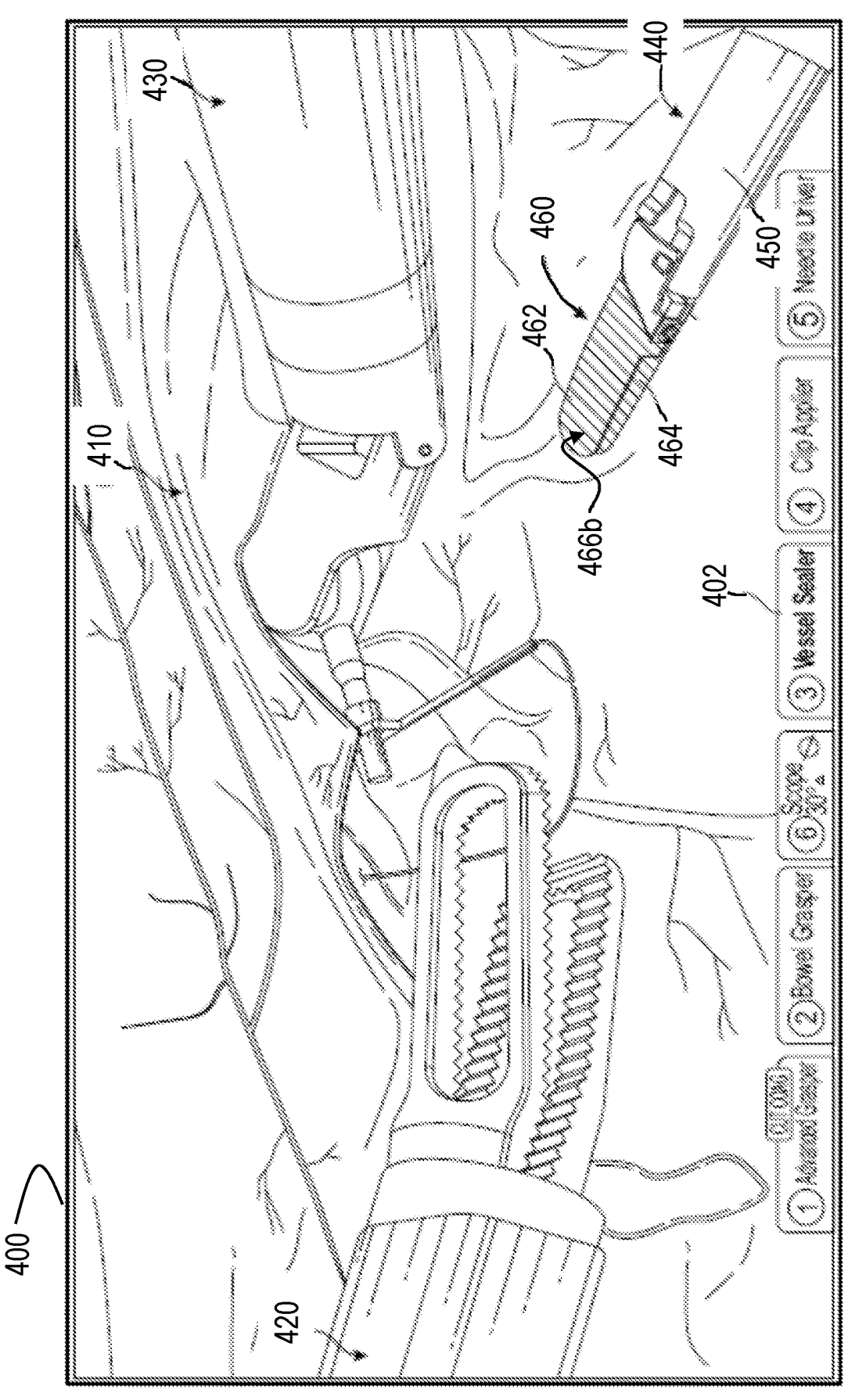
FIG. 8B depicts an example of the display of FIG. 8A in a second state of operation.

FIGS. 8A-8B show an example of how user feedback (block 310) may be provided visually through a display (400). In some versions, display (400) is provided via display screen (34) of console unit (30). Alternatively, display (400) may be provided by any other suitable equipment that is within the field of view of the clinician (C). Display (400) of this example provides a laparoscopic view of the surgical field (410) from a laparoscope (not shown) that is inserted in the patient. Two robotically-controlled tissue grasping instruments (420, 430) are viewable within the surgical field (410). An energy-applying surgical instrument (440) is also viewable within the surgical field. Energy-applying surgical instrument (440) of this example includes an end effector (460) at the distal end of a shaft assembly (450). End effector (460) includes a pair of jaws (462, 464). In some versions, end effector (460) is operable to apply RF electrosurgical energy to tissue, like end effector (218). In some other versions, end effector (460) is operable to apply ultrasonic energy to tissue, like end effector (250). Alternatively, end effector (460) may take any other suitable form and apply energy to tissue via any other suitable modality.

An indicator (402) at the bottom of display (400) identifies energy-applying surgical instrument (440) as a vessel sealer. Display (400) also provides an indication of the temperature state of end effector (460) through augmented reality. In particular, in the state shown in FIG. 8A, end effector (460) is within a temperature range where end effector (460) provides little to no risk of adversely affecting non-targeted tissue, other instrumentation, or a clinician (C) in the event of inadvertent contact. Thus, end effector (460) is presented in a first indication (466a), which may comprise a first color, a first visible pattern, or some other form of augmented reality-based visual indication within the laparoscopic field of view of the surgical field (410). As the operator moves energy-applying surgical instrument (440) within the surgical field (410), first indication (466a) may move with end effector (460) in real time.

In the state shown in FIG. 8B, end effector (460) is at a temperature where end effector (460) presents a risk of adversely affecting non-targeted tissue, other instrumentation, or a clinician (C) in the event of inadvertent contact. Thus, end effector (460) is presented in a second indication (466b), which may comprise a second color, a second visible pattern, or some other form of augmented reality-based visual indication within the laparoscopic field of view of the surgical field (410). By way of example only, first indication (466a) may comprise the color green while second indication (466b) may comprise the color red. As another merely illustrative example, first indication (466a) may comprise a solid color while second indication (466b) may comprise a flashing color. As the operator moves energy-applying surgical instrument (440) within the surgical field (410), second indication (466b) may move with end effector (460) in real time.

Control module (32) may toggle between first indication (466a) and second indication (466b) based on the above-described determination (block 304) of the temperature of end effector (460); and the determination (block 306) of whether it is safe to remove end effector (460) from the patient. While only two indications (466a, 466b) are described above, some variations may provide more than two indications. It should also be understood that surgical system (10) may provide (block 310) audible feedback and/or haptic feedback to the clinician (C) who is observing display (400); while also providing visual feedback to the same clinician (C) via display (400).

B. Example of On-Arm Feedback

Figure 9A:
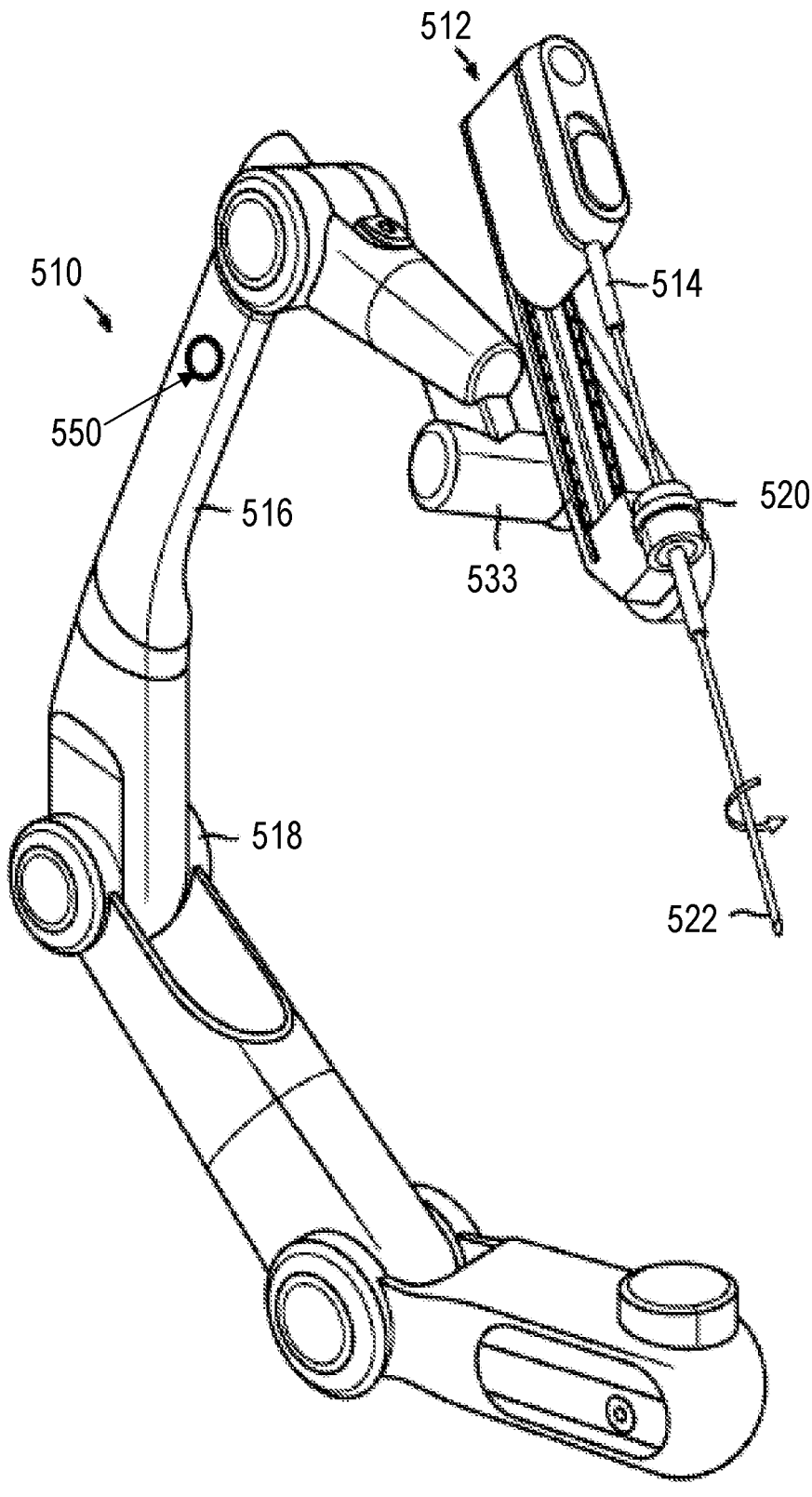
FIG. 9A depicts a perspective view of another example of a robotic arm, an example of a tool drive, and a first example of a surgical instrument, each configured for use with the robotic surgical system of FIG. 2, with an indicator in a first state.
Figure 9B:
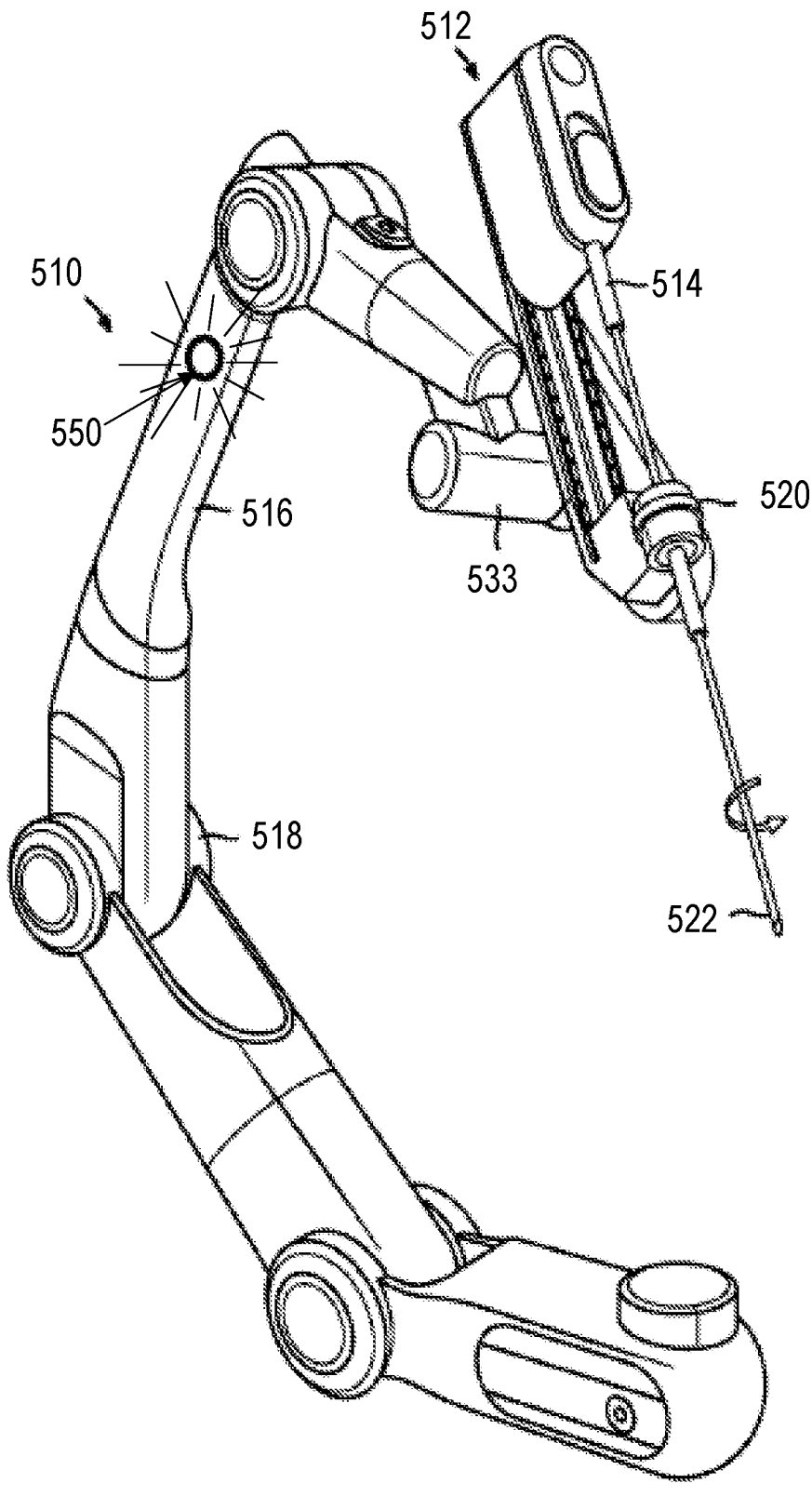
FIG. 9B depicts a perspective view of the robotic arm of FIG. 9A, with the indicator in a second state.

In the example described above with reference to FIGS. 8A-8B, a clinician (C) who is observing display (400) may readily determine in real time whether it is safe to remove end effector (460) from patient based on whether first indication (466a) or second indication (466b) is visible. However, it may also be desirable to provide (block 310) a visual indication to a clinician (C) who is not observing display (400). For instance, it may be desirable to provide (block 310) a visual indication somewhere on a robotic arm (16, 110) to indicate the temperature state of end effector (218, 250, 460). To that end, FIGS. 9A-9B show an example of a robotic arm (510) that may be used to provide (block 310) user feedback in accordance with the description above.

Robotic arm (510) of this example includes a plurality of links (516) and a plurality of joints (518) for actuating links (516) relative to one another. A tool driver (512) is attached to the distal end of robotic arm (510). Tool driver (512) includes a cannula (520) coupled to the end of tool driver (512), to receive and guide surgical instrument (514). Surgical instrument (514) may be configured and operable like any of the various surgical instruments referred to herein. Surgical instrument (514) is inserted into the patient via cannula (520). The distal end of surgical instrument (514)

includes an end effector (522). End effector (522) is configured to interact with the patient by applying energy to tissue as described herein. Joints (518) of robotic arm (510) may be actuated to selectively position and orient tool driver (512).

Robotic arm (510) of this example further includes an indicator (550). Indicator (550) of the present example comprises a light (e.g., one or more LEDs, etc.), though indicator (550) may take any other suitable visually-observable form. In the state shown in FIG. 9A, end effector (522) is within a temperature range where end effector (522) provides little to no risk of adversely affecting non-targeted tissue, other instrumentation, or a clinician (C) in the event of inadvertent contact. Indicator (550) is thus in a first visual state to visually indicate the safe temperature to the clinician (C). In the state shown in FIG. 9B, end effector (522) is at a temperature where end effector (522) presents a risk of adversely affecting non-targeted tissue, other instrumentation, or a clinician (C) in the event of inadvertent contact. Indicator (550) is thus in a second visual state to visually indicate the unsafe temperature to the clinician (C).

In some versions, the first visual state of indicator (550) comprises a non-illuminated state while the second visual state of indicator (550) comprises an illuminated state. In some other versions, the first visual state of indicator (550) comprises an illuminated state in a first color (e.g., green) while the second visual state of indicator (550) comprises an illuminated state in a second color (e.g., red). As another merely illustrative example, the first visual state of indicator (550) may comprise a non-flashing state while the second visual state of indicator (550) comprises a flashing state. Alternatively, indicator (550) may provide any other suitable forms of visual indication. It should also be understood that surgical system (10) may provide (block 310) audible feedback and/or haptic feedback to the clinician (C) who is observing robotic arm (510); while also providing visual feedback to the same clinician (C) via indicator (550). Such audible feedback and/or haptic feedback may be provided to that clinician (C) via robotic arm (510), via control console (58), and/or via any other suitable hardware.

Some versions of robotic surgical system (10) may provide (block 310) a visual indication to indicate the temperature state of end effector (218, 250, 460, 522) via display (400) without also providing (block 310) a visual indication to indicate the temperature state of end effector (218, 250, 460) via robotic arm (510). Some other versions of robotic surgical system (10) may provide (block 310) a visual indication to indicate the temperature state of end effector (218, 250, 460, 522) via robotic arm (510) without also providing (block 310) a visual indication to indicate the temperature state of end effector (218, 250, 460, 522) via display (400). Still other versions of robotic surgical system (10) may provide (block 310) a visual indication to indicate the temperature state of end effector (218, 250, 460, 522) via display (400) and also via robotic arm (510). Such versions of robotic surgical system (10) may thus simultaneously provide (block 310) a visual indication to indicate the temperature state of end effector (218, 250, 460, 522) to a first clinician (C) who is visually observing display (400) and to a second clinician (C) who is visually observing robotic arm (510).

C. Examples of Manual Arm Movement Restrictions

While the examples described above contemplate robotically driven removal of end effector (218, 250, 460, 522) from the patient, and subsequent robotically driven movement of end effector (218, 250, 460, 522) away from the patient after end effector (218, 250, 460, 522) has been removed from the patient, at least some such movement may be performed manually by a clinician (C) directly engaging robotic arm (16, 110, 510) instead of being performed robotically by a clinician (C) interacting with control module (32). For instance, while operation of end effector (218, 250, 460, 522) and robotic arm (16, 110, 510) may be driven robotically by a clinician (C) at control module (32) during a substantial portion of a surgical procedure (e.g., while end effector (218, 250, 460, 522) is disposed in the patient), at some stage of the procedure another clinician (C) may manually grasp a portion of robotic arm (16, 110) directly and thereby manually move at least a portion of robotic arm (16, 110, 510). For instance, such direct, manual manipulation of robotic arm (16, 110, 510) may occur during or shortly after removal of end effector (218, 250, 460, 522) from the patient, as at least the distal portion of robotic arm (16, 110, 510) is manually moved away from the patient and away from other robotic arms (16, 110, 510) of robotic surgical system (10). Even in cases where at least a portion of robotic arm (16, 110, 510) is directly driven manually by a clinician (C) rather than being driven robotically by a clinician via control module (32), control module (32) may still execute algorithms to prevent or reduce the risk of end effector (218, 250, 460, 522) contacting non-targeted tissue, other instrumentation, or the clinician (C) when the temperature of end effector (218, 250, 460, 522) is outside of a desirable range.

Figure 10:
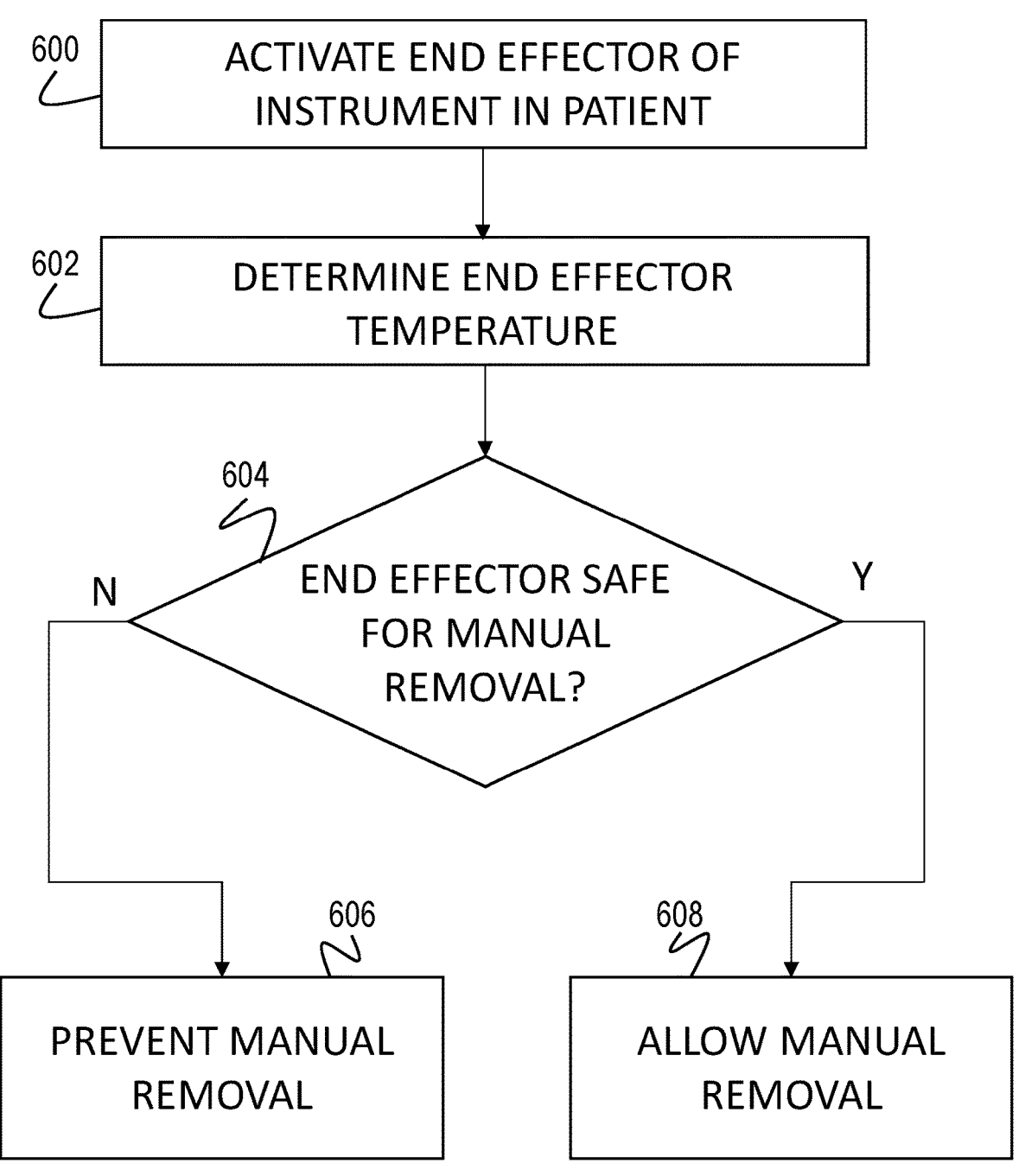
FIG. 10 depicts a flow chart showing another example of a control algorithm that may be executed by the robotic surgical system of FIG. 2.

FIG. 10 shows an example of another control algorithm that may be executed, at least in part, by control module (32) during operation of robotic surgical system (10). While the algorithm and method of operation of FIG. 10 are described herein in the context of robotic surgical system (10) described above, the same algorithm and method of operation (and variations thereof) may be carried out via other kinds of robotic surgical systems (10). In this example, the method of operation begins with end effector (218, 250, 460, 522) being activated (block 600) within the patient. As noted above, this may include applying RF electrosurgical energy to tissue, applying ultrasonic energy to tissue, applying a combination of RF and ultrasonic energy to tissue, or applying some other form of energy to tissue. As also noted above, this may eventually result in substantial heating of end effector (218, 250, 460, 522) (or substantial cooling of an end effector).

Next, control module (32) determines (block 602) the temperature of end effector (218, 250, 460, 522). This determination (block 602) may be carried out as described above with respect to the similar determination (block 304) of the algorithm shown in FIG. 7. After determining (block 602) the temperature of end effector (218, 250, 460, 522), control module (32) may determine (block 604) whether it is safe to remove end effector (218, 250, 460, 522) from the patient. This determination (block 604) may be carried out as described above with respect to the similar determination (block 306) of the algorithm shown in FIG. 7. If control module (32) determines (block 604) that it is safe to remove end effector (218, 250, 460, 522) from the patient, then control module (32) may allow (block 608) end effector (218, 250, 460, 522) to be manually removed from the patient. A clinician (C) may thus manually grasp a portion of robotic arm (16, 110, 510) and thereby manipulate robotic arm (16, 110, 510) to remove end effector (218, 250, 460, 522) from the patient.

If control module (32) determines (block 604) that it is not safe to remove end effector (218, 250, 460, 522) from the patient, then control module (32) may prevent (block 606) manual removal of end effector (218, 250, 460, 522) from the patient. To that end, control module (32) may effectively lock joints (118, 518) of robotic arm (16, 110, 510). When joints (118, 518) are effectively locked, the entirety of robotic arm (16, 110, 510) may be substantially rigid such that end effector (218, 250, 460, 522) cannot be removed from the patient. In some versions, joints (118, 518) include brake features that may be activated by control module (32) to effectively lock joints (118, 518). In some other versions, control module (32) may provide motor braking of servo motors that are used to otherwise drive movement at joints (118, 518), to thereby effectively lock joints (118, 518). Alternatively, control module (32) may effectively lock joints (118, 518) in any other suitable fashion to prevent (block 606) manual removal of end effector (218, 250, 460, 522) from the patient.

In cases where control module (32) effectively locks joints (118, 518) to prevent (block 606) manual removal of end effector (218, 250, 460, 522) from the patient, control module (32) may continuously loop back to determining (block 602) the real-time temperature of end effector (218, 250, 460, 522), determining (block 604) whether that temperature is safe for removal of end effector (218, 250, 460, 522) from the patient, and either allow (block 608) removal or maintain prevention (block 606) of removal of end effector (218, 250, 460, 522) from the patient.

Some variations of the algorithm shown in FIG. 10 allow a clinician to manually remove end effector (218, 250, 460, 522) from the patient by manually manipulating robotic arm (16, 110, 510), even if control module (32) determines (block 604) that the temperature of end effector (218, 250, 460, 522) exceeds a threshold; yet control module (32) may immediately prevent (block 606) further movement of robotic arm (16, 110, 510) as soon as end effector (218, 250, 460, 522) exits the patient. Such post-removal prevention of further movement of robotic arm (16, 110, 510) may be provided by effectively locking joints (118, 518), as described above, immediately after end effector (218, 250, 460, 522) exits the patient.

In cases where control module (32) prevents (block 606) removal of end effector (218, 250, 460, 522) from the patient in response to determining (block 604) that the temperature of end effector (218, 250, 460, 522) renders end effector (218, 250, 460, 522) unsafe for free removal from the patient, some variations may nevertheless allow the clinician (C) to override this preventing (block 606) by providing further user input clearly indicating an intent to override. Such override may be necessary in some emergency situations where immediate removal of end effector (218, 250, 460, 522) from the patient is a higher safety priority than preventing inadvertent contact between end effector (218, 250, 460, 522) and either non-targeted tissue, other instrumentation, or the clinician. In some versions where control module (32) allows an emergency override of the prevention (block 606) of the removal of end effector (218, 250, 460, 522) from the patient, control module (32) may still prevent (block 606) further movement of robotic arm (16, 110, 510) as soon as end effector (218, 250, 460, 522) exits the patient.

Figure 11:
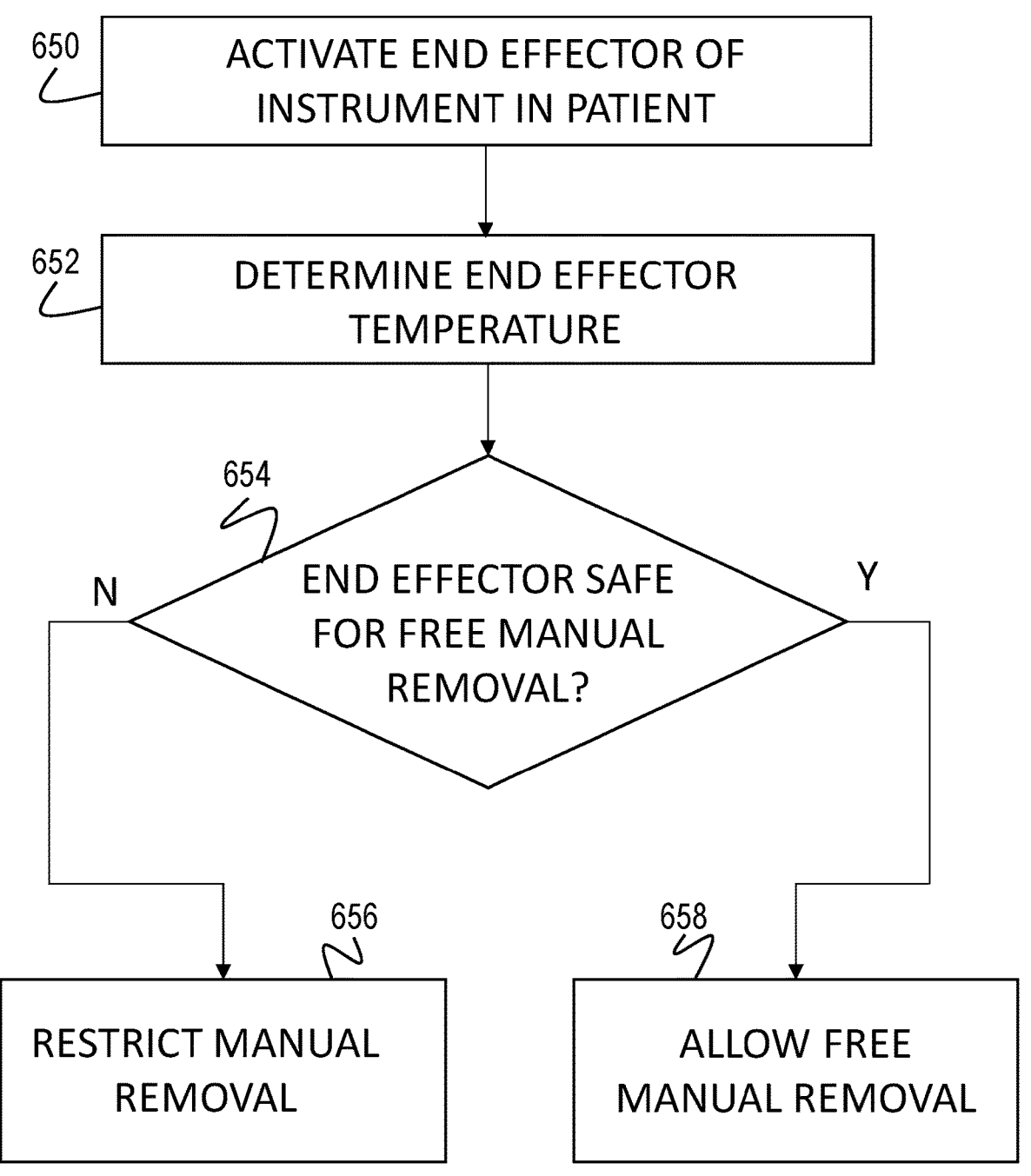
FIG. 11 depicts a flow chart showing another example of a control algorithm that may be executed by the robotic surgical system of FIG. 2.

While the algorithm described above with reference to FIG. 10 completely prevents (block 606) removal of removal of end effector (218, 250, 460, 522) from the patient when the temperature of end effector (218, 250, 460, 522) renders end effector (218, 250, 460, 522) unsafe for free removal from the patient, it may be desirable allow substantially restricted removal of end effector (218, 250, 460, 522) from the patient even when the temperature of end effector (218, 250, 460, 522) is substantially high (or substantially low). To that end, FIG. 11 shows an example of another control algorithm that may be executed, at least in part, by control module (32) during operation of robotic surgical system (10). While the algorithm and method of operation of FIG. 11 are described herein in the context of robotic surgical system (10) described above, the same algorithm and method of operation (and variations thereof) may be carried out via other kinds of robotic surgical systems (10).

In the example depicted in FIG. 11, the method of operation begins with end effector (218, 250, 460, 522) being activated (block 650) within the patient. AAs noted above, this may include applying RF electrosurgical energy to tissue, applying ultrasonic energy to tissue, applying a combination of RF and ultrasonic energy to tissue, or applying some other form of energy to tissue. As also noted above, this may eventually result in substantial heating of end effector (218, 250, 460, 522) (or substantial cooling of an end effector).

Next, control module (32) determines (block 652) the temperature of end effector (218, 250, 460, 522). This determination (block 652) may be carried out as described above with respect to the similar determination (block 304) of the algorithm shown in FIG. 7. After determining (block 652) the temperature of end effector (218, 250, 460, 522), control module (32) may determine (block 654) whether it is safe to remove end effector (218, 250, 460, 522) from the patient. This determination (block 654) may be carried out as described above with respect to the similar determination (block 306) of the algorithm shown in FIG. 7. If control module (32) determines (block 654) that it is safe to freely remove end effector (218, 250, 460, 522) from the patient, then control module (32) may allow (block 658) end effector (218, 250, 460, 522) to be manually removed from the patient in an unrestricted fashion. A clinician (C) may thus manually grasp a portion of robotic arm (16, 110, 510) and thereby manipulate robotic arm (16, 110, 510) to remove end effector (218, 250, 460, 522) from the patient, without such movement being restricted along one or more dimensions.

If control module (32) determines (block 654) that it is not safe to remove end effector (218, 250, 460, 522) from the patient, then control module (32) may restrict (block 656) manual removal of end effector (218, 250, 460, 522) from the patient while still allowing manual removal of end effector (218, 250, 460, 522) from the patient. To that end, control module (32) may restrict (block 656) movement of end effector (218, 250, 460, 522) by allowing movement of one or more portions of robotic arm (16, 110, 510) along only one or more certain dimensions while preventing movement of one or more portions of robotic arm (16, 110, 510) along only one or more other certain dimensions. For instance, control module (32) may allow a clinician (C) to manually manipulate robotic arm (16, 110, 510) to remove end effector (218, 250, 460, 522) from the patient along the same pathway along which end effector (218, 250, 460, 522) was inserted into the patient, such that the removal path is a simple reversal of the insertion path. To provide such restriction of movement, control module (32) may effectively lock and unlock one or more joints (118, 518) as described above.

In some cases, control module (32) may need to effectively lock and unlock one or more joints (118, 518) in a certain sequence to allow the allow the clinician (C) to manually manipulate robotic arm (16, 110, 510) to remove end effector (218, 250, 460, 522) from the patient along a pathway representing a reversal of the insertion path along which end effector (218, 250, 460, 522) was inserted into the patient. In such cases, control module (32) may track movement of links (116, 516) at joints (118, 518) in real time to lock and unlock the appropriate joints (118, 518) at the appropriate times. Control module (32) may track movement of links (116, 516) at joints (118, 518) based on feedback from one or more sensors in robotic arm (110, 516) and/or in any other suitable fashion.

Some variations of the algorithm shown in FIG. 11 allow a clinician to manually remove end effector (218, 250, 460, 522) from the patient by manually manipulating robotic arm (16, 110, 510) while restricting (block 656) such movement along a certain path; and then immediately prevent further movement of robotic arm (16, 110, 510) as soon as end effector (218, 250, 460, 522) exits the patient. Such post-removal prevention of further movement of robotic arm (16, 110, 510) may be provided by effectively locking joints (118, 518), as described above, immediately after end effector (218, 250, 460, 522) exits the patient. As yet another variation, in cases where control module (32) restricts (block 656) movement of end effector (218, 250, 460, 522) along a first path (e.g., the reverse of the insertion path) as end effector (218, 250, 460, 522) is removed from the patient, control module (32) may further restrict (block 656) movement of end effector (218, 250, 460, 522) along a second path after the first path is completed (i.e., after end effector (218, 250, 460, 522). For instance, the second path may be defined to avoid contact between effector (218, 250, 460, 522) and other instrumentation. In addition, or in the alternative, the second path may be defined to avoid contact between effector (218, 250, 460, 522) and the clinician (C). Such post-removal restriction of further movement of robotic arm (16, 110, 510) may be provided by sequentially locking and unlocking selected joints (118, 518), as described above, immediately after end effector (218, 250, 460, 522) exits the patient.

It should be understood that aspects of the algorithms described above with reference to FIGS. 10 and 11 may be combined with aspects of the algorithm described above with reference to FIG. 7. For instance, while preventing (block 606) manual removal of end effector (218, 250, 460, 522) from the patient, or while restricting (block 606) manual removal of end effector (218, 250, 460, 522) from the patient, control module (32) may also provide (block 310) user feedback via display (400) as described above with reference to FIGS. 8A-8B. Similarly, while preventing (block 606) manual removal of end effector (218, 250, 460, 522) from the patient, or while restricting (block 606) manual removal of end effector (218, 250, 460, 522) from the patient, control module (32) may provide (block 310) user feedback via indicator (550) as described above with reference to FIGS. 9A-9B. Control module (32) may also provide (block 310) audible feedback and/or haptic feedback to the clinician (C) while preventing (block 606) manual removal of end effector (218, 250, 460, 522) from the patient or while restricting (block 606) manual removal of end effector (218, 250, 460, 522) from the patient.

As another example of how aspects of the algorithms of FIGS. 7 and 11 may be combined, the prevention (block 312) of robotic removal of end effector (218, 250, 460, 522) from the patient may be converted to a restricted robotic removal of end effector (218, 250, 460, 522) from the patient. In other words, in response to determining (block 306) that the temperature of end effector (218, 250, 460, 522), control module (32) may allow the clinician (C) to robotically remove end effector (218, 250, 460, 522) from patient; yet restrict the removal path to a certain path (e.g., along a reversed route of the insertion path).

As yet another variation of the algorithms described above with reference to FIGS. 7 and 10-11, control module (32) may prevent a surgical instrument (6, 24, 114, 210, 440, 514) from being removed from a robotic arm (16, 110, 510) (e.g., to replace a surgical instrument (6, 24, 114, 210, 440, 514)) when control module (32) determines (blocks 306, 604, 654) that the temperature of end effector (218, 250, 460, 522) exceeds a threshold (or falls below a threshold in cases of substantially cold end effectors). In such cases, control module (32) may continue to track the temperature of end effector (218, 250, 460, 522) and then enable removal of end effector (218, 250, 460, 522) after the temperature of effector (218, 250, 460, 522) falls below the threshold (exceeds a threshold in cases of substantially cold end effectors).

Any of the teachings above may be readily combined with any of the various teachings of U.S. Pub. No. 2021/0298813, entitled "Systems and Methods of Communicating Thermal Information for Surgical Robotic Devices," published Sep. 30, 2021, now abandoned, the disclosure of which is incorporated by reference herein, in its entirety; U.S. Pub. No. 2021/0298815, entitled "Systems and Methods of Communicating Thermal Information for Surgical Robotic Devices," published Sep. 30, 2021, the disclosure of which is incorporated by reference herein, in its entirety; and/or U.S. Pub. No. 2021/0298852, entitled "Systems and Methods of Communicating Thermal Information for Surgical Robotic Devices," published Sep. 30, 2021, now abandoned, the disclosure of which is incorporated by reference herein, in its entirety.

IV. EXAMPLES OF COMBINATIONS

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system, comprising: (a) a robotic arm; (b) an instrument configured to couple with the robotic arm, the instrument having an end effector operable to apply energy to tissue of a patient; and (c) a control module, the control module being operable to drive movement of the robotic arm to thereby move the instrument relative to the patient, the control module being configured to: (i) monitor one or more parameters indicative of a temperature of a portion of the end effector, (ii) determine whether the temperature of the portion of the end effector crosses a threshold value, based at least in part on the one or more monitored parameters, and (iii) restrict movement of the end effector in response to determining that the temperature of the portion of the end effector crosses the threshold value, the restricted movement including one or both of: (A) removal of the end effector from the patient, or (B) movement of the end effector after removal of the end effector from the patient.

Example 2

The system of Example 1, the control module being further configured to restrict movement of the end effector in response to determining that the temperature of the portion of the end effector crosses the threshold value by preventing removal of the end effector from the patient.

Example 3

The system of any of Examples 1 through 2, the control module being further configured to restrict movement of the end effector in response to determining that the temperature of the portion of the end effector crosses the threshold value by preventing movement of the end effector after removal of the end effector from the patient.

Example 4

The system of any of Examples 1 through 3, the control module being further configured to restrict movement of the end effector in response to determining that the temperature of the portion of the end effector crosses the threshold value by allowing removal of the end effector only along a certain path.

Example 5

The system of Example 4, the certain path representing a reversal of an insertion path of the end effector.

Example 6

The system of any of Examples 1 through 5, the control module being further configured to restrict movement of the end effector in response to determining that the temperature of the portion of the end effector crosses the threshold value by allowing movement of the end effector only along a certain path after removal of the end effector from the patient.

Example 7

The system of any of Examples 1 through 6, the control module being further configured to prevent removal of the instrument from the robotic arm in response to determining that the temperature of the portion of the end effector crosses the threshold value.

Example 8

The system of Example 7, the console unit further including a display screen.

Example 9

The system of Example 8, the control module being further configured to provide a user notification via the display screen in response to determining that the temperature of the portion of the end effector crosses the threshold value.

Example 10

The system of Example 9, the display screen being further configured to provide a real-time laparoscopic field of view of a surgical field, the control module being further configured to provide a user notification via augmented reality within the real-time laparoscopic field of view.

Example 11

The system of Example 10, the control module being further configured to provide a user notification via augmented reality within the real-time laparoscopic field of view by providing a visual indication on a portion of the end effector disposed within the real-time laparoscopic field of view.

Example 12

The system of Example 11, the visual indication comprising one or more of a predetermined color indicating a temperature state of the portion of the end effector or a predetermined visual pattern indicating a temperature state of the portion of the end effector.

Example 13

The system of any of Examples 1 through 12, the robotic arm comprising a visual indicator, the control module being further configured to provide a user notification via the visual indicator of the robotic arm in response to determining that the temperature of the portion of the end effector crosses the threshold value.

Example 14

The system of Example 13, the visual indicator of the robotic arm comprising a light.

Example 15

The system of any of Examples 1 through 14, the control module being further configured to provide a user notification via one or both of audible feedback or haptic feedback in response to determining that the temperature of the portion of the end effector crosses the threshold value.

Example 16

The system of any of Examples 1 through 15, the end effector comprising at least one electrode, the at least one electrode being operable to apply electrosurgical energy to tissue.

Example 17

The system of any of Examples 1 through 16, the end effector comprising an ultrasonic blade, the ultrasonic blade being operable to apply ultrasonic energy to tissue.

Example 18

The system of any of Examples 1 through 17, the robotic arm comprising a plurality of links and a plurality of joints, the links being operable to pivot at the joints.

Example 19

The system of any of Examples 1 through 18, further comprising a table, the robotic arm being coupled with the table, the table being configured to support the patient.

Example 20

The system of Example 19, further comprising a plurality of additional robotic arms, the additional robotic arms being coupled with the table.

Example 21

The system of any of Examples 1 through 20, further comprising a console unit, the control module being incorporated into the console unit.

Example 22

A control module for a robotic surgical system, the control module storing instructions to perform the following: (i) monitor one or more parameters indicative of a temperature of a portion of an end effector of an instrument coupled with a robotic arm of the robotic surgical system, the end effector being operable to apply energy to tissue of a patient, (ii) determine whether the temperature of the portion of the end effector crosses a threshold value, based at least in part on the one or more monitored parameters, and (iii) restrict movement of the end effector in response to determining that the temperature of the portion of the end effector crosses the threshold value, the restricted movement including one or both of: (A) removal of the end effector from the patient, or (B) movement of the end effector after removal of the end effector from the patient.

Example 23

The control module of Example 22, the control module further storing instructions to restrict movement of the end effector in response to determining that the temperature of the portion of the end effector crosses the threshold value by either: (1) preventing removal of the end effector from the patient, or (2) allowing removal of the end effector only along a certain path.

Example 24

The control module of any of Examples 22 through 23, the control module further storing instructions to restrict movement of the end effector in response to determining that the temperature of the portion of the end effector crosses the threshold value by either: (1) preventing movement of the end effector after removal of the end effector from the patient, (2) allowing movement of the end effector only along a certain path after removal of the end effector from the patient, or (3) preventing removal of the instrument from the robotic arm of robotic surgical system.

Example 25

A method comprising: (a) monitoring one or more parameters indicative of a temperature of a portion of an end effector of an instrument coupled with a robotic arm of a robotic surgical system, the end effector being operable to apply energy to tissue of a patient; (b) determining whether the temperature of the portion of the end effector crosses a threshold value, based at least in part on the one or more monitored parameters; (c) restricting movement of the end effector in response to determining that the temperature of the portion of the end effector crosses the threshold value, the restricted movement including one or both of: (A)

removal of the end effector from the patient, or (B) movement of the end effector after removal of the end effector from the patient.

Example 26

A non-transitory computer readable storage medium storing instructions which, when executed by at least one processing unit, cause the at least one processing unit to perform the steps of the method according to Example 25.

V. MISCELLANEOUS

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator. Moreover, terms such as "upper" and "lower" are merely spatial terms relative to the figures and are not intended to unnecessarily limit the invention described herein.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components.

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those skilled in the art.

While the examples herein are described mainly in the context of instruments having RF electrodes, it should be understood that various teachings herein may be readily applied to a variety of other types of devices. By way of example only, the various teachings herein may be readily applied to other types of surgical instruments including tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those skilled in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system, comprising:
   (a) a robotic arm including a plurality of joints;
   (b) an instrument configured to couple with the robotic arm, the instrument having an end effector operable to apply energy to tissue of a patient; and
   (c) a control module, the control module being operable to drive movement of the robotic arm to thereby move the instrument relative to the patient, the control module being configured to:
      (i) monitor one or more parameters indicative of a temperature of a portion of the end effector,
      (ii) determine whether the temperature of the portion of the end effector crosses a threshold value, based at least in part on the one or more monitored parameters, and
      (iii) restrict movement of the end effector in response to determining that the temperature of the portion of the end effector crosses the threshold value, the restricted movement including allowing removal of the end effector only along a first certain path by locking the plurality of joints in a certain sequence to permit movement of the end effector along the first certain path.

2. The system of claim 1, the control module being further configured to restrict movement of the end effector in response to determining that the temperature of the portion of the end effector crosses the threshold value by temporarily preventing removal of the end effector from the patient.

3. The system of claim 1, the control module being further configured to restrict movement of the end effector in response to determining that the temperature of the portion of the end effector crosses the threshold value by preventing movement of the end effector after removal of the end effector from the patient.

4. The system of claim 1, the first certain path representing a reversal of an insertion path of the end effector.

5. The system of claim 1, the control module being further configured to restrict movement of the end effector in response to determining that the temperature of the portion of the end effector crosses the threshold value by allowing movement of the end effector only along a second certain path after removal of the end effector from the patient.

6. The system of claim 1, the control module being further configured to prevent removal of the instrument from the robotic arm in response to determining that the temperature of the portion of the end effector crosses the threshold value.

7. The system of claim 6, the control module further including a display screen.

8. The system of claim 7, the control module being further configured to provide a user notification via the display screen in response to determining that the temperature of the portion of the end effector crosses the threshold value.

9. The system of claim 8, the display screen being further configured to provide a real-time laparoscopic field of view of a surgical field, the control module being further configured to provide a user notification via augmented reality within the real-time laparoscopic field of view.

10. The system of claim 9, the control module being further configured to provide a user notification via augmented reality within the real-time laparoscopic field of view by providing a visual indication on a portion of the end effector disposed within the real-time laparoscopic field of view.

11. The system of claim 10, the visual indication comprising one or more of a predetermined color indicating a temperature state of the portion of the end effector or a predetermined visual pattern indicating a temperature state of the portion of the end effector.

12. The system of claim 1, the robotic arm comprising a visual indicator, the control module being further configured to provide a user notification via the visual indicator in response to determining that the temperature of the portion of the end effector crosses the threshold value.

13. The system of claim 12, the visual indicator of the robotic arm comprising a light.

14. The system of claim 1, the control module being further configured to provide a user notification via one or both of audible feedback or haptic feedback in response to determining that the temperature of the portion of the end effector crosses the threshold value.

15. A control module for a robotic surgical system, the control module storing instructions to perform the following:

(i) monitor one or more parameters indicative of a temperature of a portion of an end effector of an instrument coupled with a robotic arm of the robotic surgical system, the robotic arm including a plurality of joints, wherein each of the plurality of joints includes a brake feature, the end effector being operable to apply energy to tissue of a patient, (ii) determine whether the temperature of the portion of the end effector crosses a threshold value, based at least in part on the one or more monitored parameters, and (iii) restrict movement of the end effector in response to determining that the temperature of the portion of the end effector crosses the threshold value, the restricted movement including preventing removal of the end effector from the patient by activating at least one brake feature of the plurality of joints thereby locking movement of at least one of the plurality of joints.

16. The control module of claim 15, the control module further storing instructions to restrict movement of the end effector in response to determining that the temperature of the portion of the end effector crosses the threshold value by, after preventing removal of the end effector from the patient, allowing removal of the end effector only along a certain path.

17. The control module of claim 15, the control module further storing instructions to restrict movement of the end effector in response to determining that the temperature of the portion of the end effector crosses the threshold value by, after preventing removal of the end effector from the patient, either:

(1) preventing movement of the end effector after removal of the end effector from the patient, or (2) allowing movement of the end effector only along a certain path after removal of the end effector from the patient, or (3) preventing removal of the instrument from the robotic arm of the robotic surgical system.

18. A method comprising:

(a) monitoring one or more parameters indicative of a temperature of a portion of an end effector of an instrument coupled with a robotic arm of a robotic surgical system, the robotic arm including a plurality of joints, with each of the plurality of joints including a servo motor to drive movement at the plurality of joints, the end effector being operable to apply energy to tissue of a patient;

(b) determining whether the temperature of the portion of the end effector crosses a threshold value, based at least in part on the one or more monitored parameters; and (c) restricting movement of the end effector in response to determining that the temperature of the portion of the end effector crosses the threshold value by a control module allowing removal of the end effector from the patient along only a certain path by effecting a motor brake of the servo motor at each of the plurality of joints, the certain path being a reversal of the path in which the end effector was inserted into the patient.

19. A non-transitory computer readable storage medium storing instructions which, when executed by at least one processing unit, cause the at least one processing unit to perform the steps of the method according to claim 18.

* * * * *